United States Patent
Nohr et al.

(10) Patent No.: US 6,242,057 B1
(45) Date of Patent: Jun. 5, 2001

(54) PHOTOREACTOR COMPOSITION AND APPLICATIONS THEREFOR

(75) Inventors: Ronald Sinclair Nohr, Alpharetta; John Gavin MacDonald, Decatur, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/070,126

(22) Filed: Apr. 29, 1998

Related U.S. Application Data

(63) Continuation of application No. 08/649,755, filed on May 29, 1996, now abandoned, which is a continuation-in-part of application No. 08/625,737, filed on Mar. 29, 1996, now abandoned, which is a continuation-in-part of application No. 08/537,593, filed on Oct. 2, 1995, now abandoned, and a continuation-in-part of application No. 08/463,188, filed on Jun. 5, 1995, now Pat. No. 5,739,175, and a continuation-in-part of application No. 08/327,077, filed on Oct. 21, 1994, now abandoned, which is a continuation-in-part of application No. 08/268,685, filed on Jun. 30, 1994, now abandoned.

(51) Int. Cl.⁷ .................... C08F 2/50; C08J 7/04; G03C 1/73; B32B 27/02; C03C 17/00
(52) U.S. Cl. .............. 427/513; 427/511; 427/519; 428/378; 430/281.1; 430/284.1; 442/149; 442/164; 522/34; 522/2; 522/42; 522/55; 522/49; 522/96; 522/173; 522/71; 522/75; 522/81; 522/36; 522/38; 522/40; 522/41; 522/43; 522/44; 522/45; 522/50; 522/57; 522/64; 523/160; 156/275.5
(58) Field of Search .................... 522/34, 36, 38, 522/64, 40, 41, 42, 43, 44, 45, 2, 49, 50, 57, 17, 27, 71, 75, 96, 173; 523/160; 427/511, 513, 519; 428/378; 442/149, 164; 430/281.1, 284.1; 156/275.5

(56) References Cited

U.S. PATENT DOCUMENTS

| | | |
|---|---|---|
| 28,225 | 11/1860 | Heseltine et al. . |
| 28,789 | 4/1860 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |

(List continued on next page.)

FOREIGN PATENT DOCUMENTS

| | | |
|---|---|---|
| 103085 | 4/1937 | (AU) . |
| 12624/88 | 9/1988 | (AU) . |
| 413257 | 10/1932 | (CA) . |
| 458808 | 12/1936 | (CA) . |
| 460268 | 10/1949 | (CA) . |
| 461082 | 11/1949 | (CA) . |
| 463021 | 2/1950 | (CA) . |
| 463022 | 2/1950 | (CA) . |
| 465495 | 5/1950 | (CA) . |
| 465496 | 5/1950 | (CA) . |
| 465499 | 5/1950 | (CA) . |
| 483214 | 5/1952 | (CA) . |
| 517364 | 10/1955 | (CA) . |
| 537687 | 3/1957 | (CA) . |

(List continued on next page.)

OTHER PUBLICATIONS

U.S. Patent application Ser. No. 08/103,503, filed Aug. 5, 1993.
U.S. Patent application Ser. No. 08/119,912, filed Sep. 10, 1993.
U.S. Patent application Ser. No. 08/183,683, filed Jan. 19, 1994.
U.S. Patent application Ser. No. 08/258,858, filed Jun. 13, 1994.
U.S. Patent application Ser. No. 08/268,685, filed Jun. 30, 1994.
U.S. Patent application Ser. No. 08/327,077, filed Oct. 21, 1994.
U.S. Patent application Ser. No. 08/336,813, filed Nov. 9, 1994.
U.S. Patent application Ser. No. 08/359,670, filed Dec. 20, 1994.
U.S. Patent application Ser. No. 08/360,501, filed Dec. 21, 1994.
U.S. Patent application Ser. No. 08/373,958, filed Jan. 17, 1995.
U.S. Patent application Ser. No. 08/393,089, filed Feb. 22, 1995.
U.S. Patent application Ser. No. 08/403,240, filed Mar. 10, 1995.
U.S. Patent application Ser. No. 08/444,670, filed May 19, 1995.
U.S. Patent application Ser. No. 08/444,780, filed May 19, 1995.

(List continued on next page.)

Primary Examiner—Susan W. Berman
(74) Attorney, Agent, or Firm—Kilpatrick Stockton LLP

(57) ABSTRACT

A method of generating reactive species which includes exposing a wavelength specific photoreactor composition to radiation, in which the wavelength specific photoreactor composition comprises one or more wavelength-specific sensitizers associated with one or more reactive species-generating photoinitiators. Also described are methods of polymerizing unsaturated monomers, methods of curing an unsaturated oligomer/monomer mixture, and methods of laminating.

27 Claims, 3 Drawing Sheets

U.S. PATENT DOCUMENTS

| | | |
|---|---|---|
| 1,955,898 | 4/1934 | Wendt et al. . |
| 1,962,111 | 6/1934 | Bamberger . |
| 2,005,378 | 6/1935 | Kiel . |
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,320,080 | 5/1967 | Mazzarella et al. . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |

| | | | | | |
|---|---|---|---|---|---|
| 3,676,690 | 7/1972 | McMillin et al. . | 4,190,671 | 2/1980 | Vanstone et al. . |
| 3,678,044 | 7/1972 | Adams . | 4,197,080 | 4/1980 | Mee . |
| 3,689,565 | 9/1972 | Hoffmann et al. . | 4,199,420 | 4/1980 | Photis . |
| 3,694,241 | 9/1972 | Guthrie et al. . | 4,229,172 | 10/1980 | Baumann et al. . |
| 3,695,879 | 10/1972 | Laming et al. . | 4,232,106 | 11/1980 | Iwasaki et al. . |
| 3,697,280 | 10/1972 | Strilko . | 4,238,492 | 12/1980 | Majoie . |
| 3,705,043 | 12/1972 | Zablak . | 4,239,843 | 12/1980 | Hara et al. . |
| 3,707,371 | 12/1972 | Files . | 4,239,850 | 12/1980 | Kita et al. . |
| 3,729,313 | 4/1973 | Smith . | 4,241,155 | 12/1980 | Hara et al. . |
| 3,737,628 | 6/1973 | Azure . | 4,242,430 | 12/1980 | Hara et al. . |
| 3,765,896 | 10/1973 | Fox . | 4,242,431 | 12/1980 | Hara et al. . |
| 3,775,130 | 11/1973 | Enomoto et al. . | 4,245,018 | 1/1981 | Hara et al. . |
| 3,788,849 | 1/1974 | Taguchi et al. . | 4,245,995 | 1/1981 | Hugl et al. . |
| 3,799,773 | 3/1974 | Watarai et al. . | 4,246,330 | 1/1981 | Hara et al. . |
| 3,800,439 | 4/1974 | Sokolski et al. . | 4,248,949 | 2/1981 | Hara et al. . |
| 3,801,329 | 4/1974 | Sandner et al. . | 4,250,096 | 2/1981 | Kvita et al. . |
| 3,817,752 | 6/1974 | Laridon et al. . | 4,251,622 | 2/1981 | Kimoto et al. . |
| 3,840,338 | 10/1974 | Zviak et al. . | 4,254,195 | 3/1981 | Hara et al. . |
| 3,844,790 | 10/1974 | Chang et al. . | 4,256,493 | 3/1981 | Yokoyama et al. . |
| 3,870,524 | 3/1975 | Watanabe et al. . | 4,256,817 | 3/1981 | Hara et al. . |
| 3,873,500 | 3/1975 | Kato et al. . | 4,258,123 | 3/1981 | Nagashima et al. . |
| 3,876,496 | 4/1975 | Lozano . | 4,258,367 | 3/1981 | Mansukhani . |
| 3,887,450 | 6/1975 | Gilano et al. . | 4,259,432 | 3/1981 | Kondoh et al. . |
| 3,895,949 | 7/1975 | Akamatsu . | 4,262,936 | 4/1981 | Miyamoto . |
| 3,901,779 | 8/1975 | Mani . | 4,268,605 | 5/1981 | Hara et al. . |
| 3,910,993 | 10/1975 | Avar et al. . | 4,268,667 | 5/1981 | Anderson . |
| 3,914,165 | 10/1975 | Gaske . | 4,269,926 | 5/1981 | Hara et al. . |
| 3,914,166 | 10/1975 | Rudolph et al. . | 4,270,130 | 5/1981 | Houle et al. . |
| 3,915,824 | 10/1975 | McGinniss . | 4,271,252 | 6/1981 | Hara et al. . |
| 3,919,323 | 11/1975 | Houlihan et al. . | 4,271,253 | 6/1981 | Hara et al. . |
| 3,926,641 | 12/1975 | Rosen . | 4,272,244 | 6/1981 | Schlick . |
| 3,928,264 | 12/1975 | Young, Jr. et al. . | 4,276,211 | 6/1981 | Singer et al. . |
| 3,933,682 | 1/1976 | Bean . | 4,277,497 | 7/1981 | Fromantin . |
| 3,952,129 | 4/1976 | Matsukawa et al. . | 4,279,653 | 7/1981 | Makishima et al. . |
| 3,960,685 | 6/1976 | Sano et al. . | 4,279,982 | 7/1981 | Iwasaki et al. . |
| 3,965,157 | 6/1976 | Harrison . | 4,279,985 | 7/1981 | Nonogaki et al. . |
| 3,978,132 | 8/1976 | Houlihan et al. . | 4,284,485 | 8/1981 | Berner . |
| 3,984,248 | 10/1976 | Sturmer . | 4,288,631 | 9/1981 | Ching . |
| 3,988,154 | 10/1976 | Sturmer . | 4,289,844 | 9/1981 | Specht et al. . |
| 4,004,998 | 1/1977 | Rosen . | 4,290,870 | 9/1981 | Kondoh et al. . |
| 4,012,256 | 3/1977 | Levinos . | 4,293,458 | 10/1981 | Gruenberger et al. . |
| 4,017,652 | 4/1977 | Gruber . | 4,298,679 | 11/1981 | Shinozaki et al. . |
| 4,022,674 | 5/1977 | Rosen . . | 4,300,123 | 11/1981 | McMillin et al. . |
| 4,024,324 | 5/1977 | Sparks . | 4,301,223 | 11/1981 | Nakamura et al. . |
| 4,039,332 | 8/1977 | Kokelenberg et al. . | 4,302,606 | 11/1981 | Barabas et al. . |
| 4,043,819 | 8/1977 | Baumann . | 4,306,014 | 12/1981 | Kunikane et al. . |
| 4,048,034 | 9/1977 | Martan . | 4,307,182 | 12/1981 | Dalzell et al. . |
| 4,054,719 | 10/1977 | Cordes, III . | 4,308,400 | 12/1981 | Felder et al. . |
| 4,056,665 | 11/1977 | Tayler et al. . | 4,315,807 | 2/1982 | Felder et al. . |
| 4,058,400 | 11/1977 | Crivello . | 4,318,705 | 3/1982 | Nowak et al. . |
| 4,067,892 | 1/1978 | Thorne et al. . | 4,318,791 | 3/1982 | Felder et al. . |
| 4,071,424 | 1/1978 | Dart et al. . | 4,321,118 | 3/1982 | Felder et al. . |
| 4,073,968 | 2/1978 | Miyamoto et al. . | 4,335,054 | 6/1982 | Blaser et al. . |
| 4,077,769 | 3/1978 | Garcia . | 4,335,055 | 6/1982 | Blaser et al. . |
| 4,079,183 | 3/1978 | Green . | 4,336,323 | 6/1982 | Winslow . |
| 4,085,062 | 4/1978 | Virgilio et al. . | 4,343,891 | 8/1982 | Aasen et al. . |
| 4,090,877 | 5/1978 | Streeper . | 4,345,011 | 8/1982 | Drexhage . |
| 4,100,047 | 7/1978 | McCarty . | 4,347,111 | 8/1982 | Gehlhaus et al. . |
| 4,105,572 | 8/1978 | Gorondy . | 4,349,617 | 9/1982 | Kawashiri et al. . |
| 4,107,733 | 8/1978 | Schickedanz . | 4,350,753 | 9/1982 | Shelnut et al. . |
| 4,110,112 | 8/1978 | Roman et al. . | 4,351,893 | 9/1982 | Anderson . |
| 4,111,699 | 9/1978 | Krueger . | 4,356,255 | 10/1982 | Tachikawa et al. . |
| 4,114,028 | 9/1978 | Baio et al. . | 4,357,468 | 11/1982 | Szejtli et al. . |
| 4,126,412 | 11/1978 | Masson et al. . | 4,359,524 | 11/1982 | Masuda et al. . |
| 4,141,807 | 2/1979 | Via . | 4,362,806 | 12/1982 | Whitmore . |
| 4,144,156 | 3/1979 | Kuesters et al. . | 4,367,072 | 1/1983 | Vogtle et al. . |
| 4,148,658 | 4/1979 | Kondoh et al. . | 4,367,280 | 1/1983 | Kondo et al. . |
| 4,162,162 | 7/1979 | Dueber . | 4,369,283 | 1/1983 | Altschuler . |
| 4,171,977 | 10/1979 | Hasegawa et al. . | 4,370,401 | 1/1983 | Winslow et al. . |
| 4,179,577 | 12/1979 | Green . | 4,372,582 | 2/1983 | Geisler . |
| 4,181,807 | 1/1980 | Green . | 4,373,017 | 2/1983 | Masukawa et al. . |

| Patent No. | Date | Name |
|---|---|---|
| 4,373,020 | 2/1983 | Winslow . |
| 4,374,984 | 2/1983 | Eichler et al. . |
| 4,376,887 | 3/1983 | Greenaway et al. . |
| 4,383,835 | 5/1983 | Preuss et al. . |
| 4,390,616 | 6/1983 | Sato et al. . |
| 4,391,867 | 7/1983 | Derick et al. . |
| 4,399,209 | 8/1983 | Sanders et al. . |
| 4,400,173 | 8/1983 | Beavan . |
| 4,401,470 | 8/1983 | Bridger . |
| 4,416,961 | 11/1983 | Drexhage . |
| 4,421,559 | 12/1983 | Owatari . |
| 4,424,325 | 1/1984 | Tsunoda et al. . |
| 4,425,162 | 1/1984 | Sugiyama . |
| 4,425,424 | 1/1984 | Altland et al. . |
| 4,426,153 | 1/1984 | Libby et al. . |
| 4,434,035 | 2/1984 | Eichler et al. . |
| 4,440,827 | 4/1984 | Miyamoto et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,477,681 | 10/1984 | Gehlhaus et al. . |
| 4,489,334 | 12/1984 | Owatari . |
| 4,495,041 | 1/1985 | Goldstein . |
| 4,496,447 | 1/1985 | Eichler et al. . |
| 4,500,355 | 2/1985 | Shimada et al. . |
| 4,508,570 | 4/1985 | Fugii et al. . |
| 4,510,392 | 4/1985 | Litt et al. . |
| 4,523,924 | 6/1985 | Lacroix . |
| 4,524,122 | 6/1985 | Weber et al. . |
| 4,534,838 | 8/1985 | Lin et al. . |
| 4,548,896 | 10/1985 | Sabongi et al. . |
| 4,555,474 | 11/1985 | Kawamura . |
| 4,557,730 | 12/1985 | Bennett et al. . |
| 4,564,560 | 1/1986 | Tani et al. . |
| 4,565,769 | 1/1986 | Dueber et al. . |
| 4,567,171 | 1/1986 | Mangum . |
| 4,571,377 | 2/1986 | McGinniss et al. . |
| 4,595,745 | 6/1986 | Nakano et al. . |
| 4,604,344 | 8/1986 | Irving et al. . |
| 4,605,442 | 8/1986 | Kawashita et al. . |
| 4,613,334 | 9/1986 | Thomas et al. . |
| 4,614,723 | 9/1986 | Schmidt et al. . |
| 4,617,380 | 10/1986 | Hinson et al. . |
| 4,620,875 | 11/1986 | Shimada et al. . |
| 4,620,876 | 11/1986 | Fugii et al. . |
| 4,622,286 | 11/1986 | Sheets . |
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,713,113 | 12/1987 | Shimada et al. . |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,771,802 | 9/1988 | Tannenbaum . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al. . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,944,988 | 7/1990 | Yasuda et al. . |
| 4,950,304 | 8/1990 | Reinert et al. . |
| 4,952,478 | 8/1990 | Miyagawa et al. . |
| 4,952,680 | 8/1990 | Schmeidl . |
| 4,954,380 | 9/1990 | Kanome et al. . |
| 4,954,416 | 9/1990 | Wright et al. . |
| 4,956,254 | 9/1990 | Washizu et al. . |

| | | |
|---|---|---|
| 4,964,871 | 10/1990 | Reinert et al. . |
| 4,965,294 | 10/1990 | Ohngemach et al. . |
| 4,966,607 | 10/1990 | Shinoki et al. . |
| 4,966,833 | 10/1990 | Inoue . |
| 4,968,596 | 11/1990 | Inoue et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,988,561 | 1/1991 | Wason . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,017,195 | 5/1991 | Satou et al. . |
| 5,023,129 | 6/1991 | Morganti et al. . |
| 5,025,036 | 6/1991 | Carson et al. . |
| 5,026,425 | 6/1991 | Hindagolla et al. . |
| 5,026,427 | 6/1991 | Mitchell et al. . |
| 5,028,262 | 7/1991 | Barlow, Jr. et al. . |
| 5,028,792 | 7/1991 | Mullis . |
| 5,030,243 | 7/1991 | Reinert . |
| 5,030,248 | 7/1991 | Meszaros . |
| 5,034,526 | 7/1991 | Bonham et al. . |
| 5,037,726 | 8/1991 | Kojima et al. . |
| 5,045,435 | 9/1991 | Adams et al. . |
| 5,045,573 | 9/1991 | Kohler et al. . |
| 5,047,556 | 9/1991 | Kohler et al. . |
| 5,049,777 | 9/1991 | Mechtersheimer . |
| 5,053,320 | 10/1991 | Robbillard . |
| 5,055,579 | 10/1991 | Pawlowski et al. . |
| 5,057,562 | 10/1991 | Reinert . |
| 5,068,364 | 11/1991 | Takagaki et al. . |
| 5,069,681 | 12/1991 | Bouwknegt et al. . |
| 5,070,001 | 12/1991 | Stahlhofen . |
| 5,073,448 | 12/1991 | Vieira et al. . |
| 5,074,885 | 12/1991 | Reinert . |
| 5,076,808 | 12/1991 | Hahn et al. . |
| 5,085,698 | 2/1992 | Ma et al. . |
| 5,087,550 | 2/1992 | Blum et al. . |
| 5,089,050 | 2/1992 | Vieira et al. . |
| 5,089,374 | 2/1992 | Saeva . |
| 5,096,456 | 3/1992 | Reinert etal. . |
| 5,096,489 | 3/1992 | Laver . |
| 5,096,781 | 3/1992 | Vieira et al. . |
| 5,098,477 | 3/1992 | Vieira et al. . |
| 5,098,793 | 3/1992 | Rohrbach et al. . |
| 5,098,806 | 3/1992 | Robillard . |
| 5,106,723 | 4/1992 | West et al. . |
| 5,108,505 | 4/1992 | Moffat . |
| 5,108,874 | 4/1992 | Griffing et al. . |
| 5,110,706 | 5/1992 | Yumoto et al. . |
| 5,110,709 | 5/1992 | Aoai et al. . |
| 5,114,832 | 5/1992 | Zertani et al. . |
| 5,124,723 | 6/1992 | Laver . |
| 5,130,227 | 7/1992 | Wade et al. . |
| 5,133,803 | 7/1992 | Moffatt . |
| 5,135,940 | 8/1992 | Belander et al. . |
| 5,139,572 | 8/1992 | Kawashima . |
| 5,139,687 | 8/1992 | Borgher, Sr. et al. . |
| 5,141,556 | 8/1992 | Matrick . |
| 5,141,797 | 8/1992 | Wheeler . |
| 5,144,964 | 9/1992 | Demian . |
| 5,147,901 | 9/1992 | Rutsch et al. . |
| 5,153,104 | 10/1992 | Rossman et al. . |
| 5,153,105 | 10/1992 | Sher et al. . |
| 5,153,166 | 10/1992 | Jain et al. . |
| 5,160,346 | 11/1992 | Fuso et al. . |
| 5,160,372 | 11/1992 | Matrick . |
| 5,166,041 | 11/1992 | Murofushi et al. . |
| 5,169,436 | 12/1992 | Matrick . |
| 5,169,438 | 12/1992 | Matrick . |
| 5,173,112 | 12/1992 | Matrick et al. . |
| 5,176,984 | 1/1993 | Hipps, Sr. et al. . |
| 5,178,420 | 1/1993 | Shelby . |
| 5,180,425 | 1/1993 | Matrick et al. . |
| 5,180,624 | 1/1993 | Kojima et al. . |
| 5,180,652 | 1/1993 | Yamaguchi et al. . |
| 5,181,935 | 1/1993 | Reinert et al. . |
| 5,185,236 | 2/1993 | Shiba et al. . |
| 5,187,045 | 2/1993 | Bonham et al. . |
| 5,187,049 | 2/1993 | Sher et al. . |
| 5,190,565 | 3/1993 | Berenbaum et al. . |
| 5,190,710 | 3/1993 | Kletecka . |
| 5,190,845 | 3/1993 | Hashimoto et al. . |
| 5,193,854 | 3/1993 | Borowski, Jr. et al. . |
| 5,196,295 | 3/1993 | Davis . |
| 5,197,991 | 3/1993 | Rembold . |
| 5,198,330 | 3/1993 | Martic et al. . |
| 5,202,209 | 4/1993 | Winnik et al. . |
| 5,202,210 | 4/1993 | Matsuoka et al. . |
| 5,202,211 | 4/1993 | Vercoulen . |
| 5,202,212 | 4/1993 | Shin et al. . |
| 5,202,213 | 4/1993 | Nakahara et al. . |
| 5,202,215 | 4/1993 | Kanakura et al. . |
| 5,202,221 | 4/1993 | Imai et al. . |
| 5,205,861 | 4/1993 | Matrick . |
| 5,208,136 | 5/1993 | Zanoni et al. . |
| 5,209,814 | 5/1993 | Felten et al. . |
| 5,219,703 | 6/1993 | Bugner et al. . |
| 5,221,334 | 6/1993 | Ma et al. . |
| 5,224,197 | 6/1993 | Zanoni et al. . |
| 5,224,476 | 7/1993 | Schultz et al. . |
| 5,224,987 | 7/1993 | Matrick . |
| 5,226,957 | 7/1993 | Wickramanayake et al. . |
| 5,227,022 | 7/1993 | Leonhardt et al. . |
| 5,241,059 | 8/1993 | Yoshinaga . |
| 5,244,476 | 9/1993 | Schulz et al. . |
| 5,250,109 | 10/1993 | Chan et al. . |
| 5,254,429 | 10/1993 | Gracia et al. . |
| 5,256,193 | 10/1993 | Winnik et al. . |
| 5,258,274 | 11/1993 | Helland et al. . |
| 5,261,953 | 11/1993 | Vieira et al. . |
| 5,262,276 | 11/1993 | Kawamura . |
| 5,268,027 | 12/1993 | Chan et al. . |
| 5,270,078 | 12/1993 | Walker et al. . |
| 5,271,764 | 12/1993 | Winnik et al. . |
| 5,271,765 | 12/1993 | Ma . |
| 5,272,201 | 12/1993 | Ma et al. . |
| 5,275,646 | 1/1994 | Marshall et al. . |
| 5,279,652 | 1/1994 | Kaufmann et al. . |
| 5,282,894 | 2/1994 | Albert et al. . |
| 5,284,734 | 2/1994 | Blum et al. . |
| 5,286,286 | 2/1994 | Winnik et al. . |
| 5,286,288 | 2/1994 | Tobias et al. . |
| 5,294,528 | 3/1994 | Furutachi . |
| 5,296,275 | 3/1994 | Goman et al. . |
| 5,296,556 | 3/1994 | Frihart . |
| 5,298,030 | 3/1994 | Burdeska et al. . |
| 5,300,403 | 4/1994 | Angelopolus et al. . |
| 5,300,654 | 4/1994 | Nakajima et al. . |
| 5,302,195 | 4/1994 | Helbrecht . |
| 5,302,197 | 4/1994 | Wickramanayake et al. . |
| 5,310,778 | 5/1994 | Shor et al. . |
| 5,312,713 | 5/1994 | Yokoyama et al. . |
| 5,312,721 | 5/1994 | Gesign . |
| 5,324,349 | 6/1994 | Sano et al. . |
| 5,328,504 | 7/1994 | Ohnishi . |
| 5,330,860 | 7/1994 | Grot et al. . |
| 5,334,455 | 8/1994 | Noren et al. . |

| | | |
|---|---|---|
| 5,338,319 | 8/1994 | Kaschig et al. . |
| 5,340,631 | 8/1994 | Matsuzawa et al. . |
| 5,340,854 | 8/1994 | Martic et al. . |
| 5,344,483 | 9/1994 | Hinton . |
| 5,356,464 | 10/1994 | Hickman et al. . |
| 5,362,592 | 11/1994 | Murofushi et al. . |
| 5,368,689 | 11/1994 | Agnemo . |
| 5,372,387 | 12/1994 | Wajda . |
| 5,372,917 | 12/1994 | Tsuchida et al. . |
| 5,374,335 | 12/1994 | Lindgren et al. . |
| 5,376,503 | 12/1994 | Audett et al. . |
| 5,383,961 | 1/1995 | Bauer et al. . |
| 5,384,186 | 1/1995 | Trinh . |
| 5,393,580 | 2/1995 | Ma et al. . |
| 5,401,303 | 3/1995 | Stoffel et al. . |
| 5,401,562 | 3/1995 | Akao . |
| 5,415,686 | 5/1995 | Kurabayashi et al. . |
| 5,415,976 | 5/1995 | Ali . |
| 5,424,407 | 6/1995 | Tanaka et al. . |
| 5,425,978 | 6/1995 | Berneth et al. . |
| 5,426,164 | 6/1995 | Babb et al. . |
| 5,427,415 | 6/1995 | Chang . |
| 5,429,628 | 7/1995 | Trinh et al. . |
| 5,431,720 | 7/1995 | Nagai et al. . |
| 5,432,274 | 7/1995 | Luong et al. . |
| 5,445,651 | 8/1995 | Thoen et al. . |
| 5,445,842 | 8/1995 | Tanaka et al. . |
| 5,455,143 | 10/1995 | Ali . |
| 5,459,014 | 10/1995 | Nishijima et al. . |
| 5,464,472 | 11/1995 | Horn et al. . |
| 5,466,283 | 11/1995 | Kondo et al. . |
| 5,474,691 | 12/1995 | Severns . |
| 5,475,080 | 12/1995 | Gruber et al. . |
| 5,476,540 | 12/1995 | Shields et al. . |
| 5,479,949 | 1/1996 | Battard et al. . |
| 5,489,503 | 2/1996 | Toan . |
| 5,498,345 | 3/1996 | Jollenbeck et al. . |
| 5,501,774 | 3/1996 | Burke . |
| 5,503,664 | 4/1996 | Sano et al. . |
| 5,509,957 | 4/1996 | Toan et al. . |
| 5,531,821 | 7/1996 | Wu . |
| 5,532,112 | 7/1996 | Kohler et al. . |
| 5,541,633 | 7/1996 | Winnik et al. . |
| 5,543,459 | 8/1996 | Hartmann et al. . |
| 5,569,529 | 10/1996 | Becker et al. . |
| 5,571,313 | 11/1996 | Mafune et al. . |
| 5,575,891 | 11/1996 | Trokhan et al. . |
| 5,580,369 | 12/1996 | Belding et al. . |
| 5,591,489 | 1/1997 | Dragner et al. . |
| 5,607,803 | 3/1997 | Murofushi et al. . |
| 5,635,297 | 6/1997 | Ogawa et al. . |
| 5,643,631 | 7/1997 | Donigian et al. . |
| 5,672,392 | 9/1997 | De Clercq et al. . |
| 5,681,380 | 10/1997 | Nohr et al. . |
| 5,700,582 | 12/1997 | Sargeant et al. . |
| 5,705,247 | 1/1998 | Arai et al. . |
| 5,709,976 | 1/1998 | Malhotra . |

FOREIGN PATENT DOCUMENTS

| | | |
|---|---|---|
| 552565 | 2/1958 | (CA) . |
| 571792 | 3/1959 | (CA) . |
| 779239 | 2/1968 | (CA) . |
| 930103 | 7/1973 | (CA) . |
| 2053094 | 4/1992 | (CA) . |
| 0003884 | 9/1979 | (EP) . |
| 0029284 | 5/1981 | (EP) . |
| 0127574 | 12/1984 | (EP) . |
| 0223587 | 5/1987 | (EP) . |
| 0262533 | 4/1988 | (EP) . |
| 0280458 | 8/1988 | (EP) . |
| 0308274 | 3/1989 | (EP) . |
| 0458140A1 | 10/1991 | (EP) . |
| 0458140 | 11/1991 | (EP) . |
| 0468465 | 1/1992 | (EP) . |
| 0542286 | 5/1993 | (EP) . |
| 000571190 | 11/1993 | (EP) . |
| 0608433 | 8/1994 | (EP) . |
| 0609159 | 8/1994 | (EP) . |
| 0639664 | 2/1995 | (EP) . |
| 275245 | 10/1928 | (GB) . |
| 349339 | 5/1931 | (GB) . |
| 355686 | 8/1931 | (GB) . |
| 399753 | 10/1933 | (GB) . |
| 441085 | 1/1936 | (GB) . |
| 463515 | 4/1937 | (GB) . |
| 492711 | 9/1938 | (GB) . |
| 518612 | 3/1940 | (GB) . |
| 539912 | 9/1941 | (GB) . |
| 626727 | 7/1947 | (GB) . |
| 600451 | 4/1948 | (GB) . |
| 616362 | 1/1949 | (GB) . |
| 618616 | 2/1949 | (GB) . |
| 779389 | 7/1957 | (GB) . |
| 1372884 | 11/1974 | (GB) . |
| 2146357 | 4/1985 | (GB) . |
| 92/11295 | 7/1992 | (WO) . |
| 93/06597 | 4/1993 | (WO) . |
| 94/01503 | 1/1994 | (WO) . |
| 94/22500 | 10/1994 | (WO) . |
| 94/22501 | 10/1994 | (WO) . |
| 95/04955 | 2/1995 | (WO) . |
| 96/00740 | 1/1996 | (WO) . |
| 96/19502 | 6/1996 | (WO) . |
| 96/22335 | 7/1996 | (WO) . |

OTHER PUBLICATIONS

U.S. Patent application Ser. No. 08/453,912, filed May 30, 1995.

U.S. Patent application Ser. No. 08/456,784, filed Jun. 1, 1995.

U.S. Patent application Ser. No. 08/457,025, filed Jun. 1, 1995.

U.S. Patent application Ser. No. 08/461,365, filed Jun. 5, 1995.

U.S. Patent application Ser. No. 08/461,372, filed Jun. 5, 1995.

U.S. Patent application Ser. No. 08/461,373, filed Jun. 5, 1995.

U.S. Patent application Ser. No. 08/461,382, filed Jun. 5, 1995.

U.S. Patent application Ser. No. 08/461,445, filed Jun. 5, 1995.

U.S. Patent application Ser. No. 08/461,656, filed Jun. 5, 1995.

U.S. Patent application Ser. No. 08/461,991, filed Jun. 5, 1995.

U.S. Patent application Ser. No. 08/462,101, filed Jun. 5, 1995.

U.S. Patent application Ser. No. 08/462,103, filed Jun. 5, 1995.

U.S. Patent application Ser. No. 08/462,105, filed Jun. 5, 1995.

U.S. Patent application Ser. No. 08/462,107, filed Jun. 5, 1995.

U.S. Patent application Ser. No. 08/462,214, filed Jun. 5, 1995.

U.S. Patent application Ser. No. 08/462,217, filed Jun. 5, 1995.

U.S. Patent application Ser. No. 08/463,103, filed Jun. 5, 1995.
U.S. Patent application Ser. No. 08/463,185, filed Jun. 5, 1995.
U.S. Patent application Ser. No. 08/463,187, filed Jun. 5, 1995.
U.S. Patent application Ser. No. 08/463,188, filed Jun. 5, 1995.
U.S. Patent application Ser. No. 08/463,189, filed Jun. 5, 1995.
U.S. Patent application Ser. No. 08/463,496, filed Jun. 5, 1995.
U.S. Patent application Ser. No. 08/464,216, filed Jun. 5, 1995.
U.S. Patent application Ser. No. 08/465,376, filed Jun. 5, 1995.
U.S. Patent application Ser. No. 08/465,377, filed Jun. 5, 1995.
U.S. Patent application Ser. No. 08/465,393, filed Jun. 5, 1995.
U.S. Patent application Ser. No. 08/465,397, filed Jun. 5, 1995.
U.S. Patent application Ser. No. 08/465,655, filed Jun. 5, 1995.
U.S. Provisional application Ser. No. 60/000,570, filed Jun. 28, 1995.
U.S. Patent application Ser. No. 08/537,593, filed Oct. 2, 1995.
U.S. Patent application Ser. No. 08/563,381, filed Nov. 28, 1995.
U.S. Patent application Ser. No. 08/589,321, filed Jan. 22, 1996.
U.S. Patent application Ser. No. 08/589,449, filed Jan. 22, 1996.
U.S. Patent application Ser. No. 08/625,737, filed Mar. 29, 1996.
U.S. Patent application Ser. No. 08/627,693, filed Mar. 29, 1996.
U.S. Patent application Ser. No. 08/649,754, filed May 29, 1996.
U.S. Patent application Ser. No. 08/649,755, filed May 29, 1996.
U.S. Patent application Ser. No. 08/659,497, filed Jun. 5, 1996.
U.S. Patent application Ser. No. 08/733,086, filed Oct. 16, 1996.
U.S. Patent application Ser. No. 08/757,222, filed Nov. 27, 1996.
U.S. Patent application Ser. No. 08/769,885, filed Dec. 19, 1996.
U.S. Patent application Ser. No. 08/777,996, filed Jan. 2, 1997.
U.S. Patent application Ser. No. 08/788,863, filed Jan. 23, 1997.
U.S. Patent application Ser. No. 08/843,410, filed Apr. 15, 1997.
U.S. Patent application Ser. No. 08/839,109, filed Apr. 23, 1997.
U.S. Patent application Ser. No. 08/857,454, filed May 16, 1997.
U.S. Patent application Ser. No. 08/903,911, filed Jul. 31, 1997.
U.S. Provisional application Ser. No. 60/055,785, filed Aug. 15, 1997.
U.S. Patent application Ser. No. 08/936,449, filed Sep. 24, 1997.
U.S. Patent application Ser. No. 08/946,952, filed Oct. 8, 1997.
U.S. Provisional application Ser. No. 60/062,643, filed Oct. 22, 1997.
U.S. Patent application Ser. No. 08/979,769, filed Nov. 26, 1997.
U.S. Patent application Ser. No. 08/983,159, filed Dec. 26, 1997.
U.S. Patent application Ser. No. 08/998,464, filed Dec. 26, 1997.
U.S. Patent application Ser. No. 09/002,300, filed Dec. 31, 1997.
U.S. Provisional application Ser. No. 60/071,944, filed Jan. 20, 1998.
U.S. Provisional application Ser. No. 60/071,937, filed Jan. 20, 1998.
U.S. Patentapplication Ser. No. 09/012,064, filed Jan. 22, 1998.
U.S. Patent application Ser. No. 09/018,129, filed Feb. 3, 1998.
U.S. Patent application Ser. No. 08/951,183, filed Oct. 31, 1997.
U.S. Patent application Ser. No. 09/021,552, filed Feb. 10, 1998.
U.S. Patent application Ser. No. 09/058,385, filed Apr. 9, 1998.
U.S. Provisional application Ser. No. 60/082,143, filed Apr. 17, 1998.
U.S. Patent application Ser. No. 09/070,126, filed apr. 29, 1998.
U.S. Provisional application Ser. No. 60/087,893, filed Jun. 3, 1998.
U.S. Provisional application Ser. No. 60/087,866, filed Jun. 3, 1998.
Abstract Of Patent, JP 405132638 (Mitsubishi Kasei Corp.), May 28, 1993.
Derwent Publications Ltd., London, JP 5–125318 (Mitsubishi Kasei Corp), May 21, 1993.
Abstract Of Patent, JP 405125318 ( Mitsubishi Kasei Corp.), May 21, 1993.
Abstract of patent, JP 05–117200 (Hidefumi Hirai et al.) (May 14, 1993).
Derwent World Patents Index, JP 5117105 (Mitsui Toatsu Chem Inc.) May 14, 1993.
Derwent Publications Ltd., London, JP 05061246 (Ricoh KK), Mar. 12, 1993.
Husain, N. et al. "Cyclodextrins as mobile–phase additives in reversed–phase HPLC" *American Laboratory*, 82, 80–87, 1993.
Hamilton, D.P. "Tired of Shredding? New Ricoh Method Tries Different Tack" *Wall Street Journal*, B2, 1993.
"Cyclodextrins: A Breakthrough for Molecular Encapsulation" *American Maize Products Co. (AMAIZO)*, 1993.
Duxbury "The Photochemistry and Photophysics of Triphenylmethane Dyes in Solid Liquid Media" *Chemical Review*, 93, 381–433, 1993.
Abstract of patent, JP 04–351603 (Dec. 7, 1992).
Abstract of patent, JP 04–351602, 1992.
Derwent Publications Ltd., London, JP 404314769 (Citizen Watch Co. Ltd.), Nov. 5, 1992.
Abstract of patent, JP 04315739 1992.

Derwent Publications Ltd., London, JP 04300395 (Funai Denki KK), Oct. 23, 1992.
Derwent Publications Ltd., London, JP 404213374 (Mitsubishi Kasei Corp), Aug. 4, 1992.
Abstract of patent, JP 04–210228 1992.
Abstract Of Patent, JP 404202571 (Canon Inc.), Jul. 23, 1992.
Abstract Of Patent, JP 404202271 (Mitsubishi Kasei Corp.), Jul. 23, 1992.
Derwent Publications Ltd., London, JP 4–189877 (Seiko Epson Corp), Jul. 8, 1992.
Derwent Publications Ltd., London, JP 404189876 (Seiko Epson Corp), Jul. 8, 1992.
Abstract Of Patent, JP 404189877 (Seiko Epson Corp.), Jul. 8, 1992.
Derwent Publications Ltd., London, J,A, 4–170479 (Seiko Epson Corp), Jun. 18, 1992.
Abstract of patent, JP 04–81402, 1992.
Abstract of patent, JP 04–81401, 1992.
Kogelschatz "Silent–discharge driven excimer UV sources and their applications" *Applied Surface Science*, 410–423, 1992.
Derwent Publications, Ltd., London, JP 403269167 (Japan Wool Textile KK), Nov. 29, 1991.
Derwent Publications Ltd., London, JO 3247676 (Canon KK), Nov. 5, 1991.
Abstract of patent, JP 03–220384 1991.
Patent Abstracts of Japan, JP 03184896 (Dainippon Printing Co Ltd.) Aug. 12, 1991.
Derwent Publications Ltd., London, JP 3167270 (Mitsubishi Kasei Corp), Jul. 19, 1991.
Derwent Publications Ltd., London, JO 3167270 (Mitsubishi Kasei Corp.), Jul. 19, 1991.
Derwent Publications Ltd., London, JO 3093870 (Dainippon Ink Chem KK.), Apr. 18, 1991.
Abstract of patent, JP 06369890 1991.
Kogelschatz, U. et al. "New Excimer UV Sources for Industrial Applications" *ABB Review*, 1–10, 1991.
Abstract of patent, JP 03–41165, 1991.
"Coloring/Decoloring Agent for Tonor Use Developed" *Japan Chemical Week*, 1991.
Braithwaite, M., et al. "Formulation" *Chemistry & Technology of UV & EB Formulation for Coatings, Inks & Paints*, IV, 11–12, 1991.
*Scientific Polymer Products, Inc. Brochure* 24–31 1991.
Dietliker, K. "Photoiniators for Free Radical and Catioinc Polymerisation" *Chem & Tech of UV & EB Formulation for Coatings, Inks & Paints* III, 280, 1991.
Dietliker, K. "Photoiniators for Free Radical and Catioinc Polymerisation" *Chem & Tech of UV & EB Formulation for Coatings, Inks & Paints* III 61, 63, 229–232, 405, 414, 1991.
Esrom et al. "Large area Photochemical Dry Etching of Polymers iwth Incoherent Excimer UV Radiation" *MRS Materials Research Society*, 1–7, 1991.
"New Excimer UV Sources for Industrial Applications" *ABB Review* 391, 1–10, 1991.
Esrom et al. Excimer Laser–Induced Decomposition of Aluminum Nitride *Materials Research Society, Fall Meeting* 1–6, 1991.
Esrom et al. "Metal deposition with a windowless VUV excimer source" *Applied Surface Science*, 1–5, 1991.
Esrom "Excimer Laser–Induced Surface Activation of Aln for Electroless Metal Deposition" *Mat. Res. Sco.lSymp. Proc.* 204, 457–465, 1991.

Zhang et al. "UV–induced decompositin of adsorbed Cu–acetylacetonate films at room temperature for electroless metal plating" *Applied Surface Science*, 1–6, 1991.
"Coloring/Decoloring Agent for Tonor Use Developed" *Japan Chemical Week*, 1991.
"German company develops reuseable paper" *Pulp & Paper*, 1991.
Abstract of patent, JP 02289652, 1990.
Ohashi et al. "Molecular Mechanics Studies on Inclusion Compounds of Cyanine Dye Monomers and Dimers in Cyclodextrin Cavities," *J. Am. Chem. Soc.* 112, 5824–5830, 1990.
Kogelschatz et al. "New Incoherent Ultraviolet Excimer Sources for Photolytic Material Deposition," *Laser Und Optoelektronik*, 1990.
Patent Abstracts of Japan, JP 02141287 (Dainippon Printing Co Ltd.) May 30, 1990.
Abstract of Patent, JP 0297957, (Fuji Xerox Co., Ltd.) 1990.
Derwent Publications Ltd., London, JP 2091166 (Canon KK), Mar. 30, 1990.
Esrom et al. "Metal Deposition with Incoherent Excimer Radiation" *Mat. Res. Soc. Symp. Proc.* 158, 189–198, 1990.
Esrom "UV Excimer Laer–Induced Deposition of Palladium from palladiym Acetate Films" *Mat. Res. Soc. Symp. Proc.* 158, 109–117, 1990.
Kogelschatz, U. "Silent Discharges for the Generation of ultraviolet and vacuum ultraviolet excimer radiation" *Pure & Applied Chem.* 62, 1667–74, 1990.
Esrom et al. "Investigation of the mechanism of the UV–induced palladium depostions processf from thin solid palladium acetate films" *Applied Surface Science* 46, 158–162, 1990.
Zhang et al. "VUV synchrotron radiation processing of thin palladium acetate spin–on films for metallic surface patterning" *Applied Surface Science* 46, 153–157, 1990.
Brennan et al. "Tereoelectronic effects in ring closure reactions: the 2'–hydroxychalcone—flavanone equilibrium, and related systems," *Canadian J. Chem.* 68 (10), pp. 1780–1785, 1990.
Abstract of patent, JP 01–299083 1989.
Derwent Publications Ltd., London, J,O, 1182379 (Canon KK), Jul. 20, 1989.
Derwent Publications Ltd., London, JO 1011171 (Mitsbubishi Chem Ind. KK.), Jan. 13, 1989.
Gruber, R.J., et al. "Xerographic Materials" *Encyclopedia of Polymer Science and Engineering*, 17, 918–943, 1989.
Pappas, S.P. "Photocrosslinking" *Comph. Pol. Sci.* 6, 135–148, 1989.
Pappas, S.P. "Photoinitiated Polymerization" *Comph. Pol. Sci.* 4, 337–355, 1989.
Kirilenko, G.V. et al. "An analog of the vesicular process with amplitude modulation of the incident light beam" *Chemical Abstracts* 111 569[No. 111:12363 3b], 1989.
Esrom et al. "UV excimer laser–induced pre–nucleation of surfaces followed by electroless metallization" *Chemtronics* 4, 216–223, 1989.
Esrom et al. "VUV light–induced depostion of palladium using an incoherent Xe2* excimer source" *Chemtronics* 4, 1989.
Esrom et al. "UV Light–Induced Depostion of Copper Films" C5–719–C5–725, 1989.
Falbe et al. *Rompp Chemie Lexikon* 9, 270, 1989.
Allen, Norman S. *Photopolymerisation and Photoimaging Science and Technology* pp. 188–199; 210–239, 1989.

Derwent Publications, Ltd., London, SU 1423656 (Kherson Ind Inst), Sep. 15, 1988.
Derwent Publications, Ltd. London, EP 0280653 (Ciba GeigyAG), Aug. 31, 1988.
Abstract of patent, JP 63–190815, 1988.
Patent Abstracts of Japan, JP 63179985 (Tomoegawa Paper Co. Ltd.), Jul. 23, 1988.
Derwent World Patents Index, JP 63179977 (Tomoegawa Paper Mfg Co Ltd), Jul. 23, 1988.
Furcone, S.Y. et al. "Spin–on B14Sr3Ca3Cu4O16+x superconducting thin films from citrate precursors," *Appl. Phys. Lett.* 52(2 5), 2180–2182 1988.
Abstract of patent, JP 63–144329, 1988.
Abstract of patent, JP 63–130164 1988.
Derwent Publications, Ltd., London, J6 3112770 (Toray Ind Inc), May 17, 1988.
Derwent Publications, Ltd., London, J6 3108074 (Konishiroku Photo KK), May 12, 1988.
Derwent Publications, Ltd., London,J6 3108073 (Konishiroku Photo KK), May 12, 1988.
Abstract of patent, JP 61–77846 1988.
Abstract of patent, JP 63–73241 1988.
Abstract of patent, JP 6347762, 1988.
Abstract of patent, JP 63–47763, 1988.
Abstract of patent, JP 63–47764, 1988.
Abstract of patent, JP 63–47765, 1988.
Eliasson, B., et al. "UV Excimer Radiation from Dielectric–Barrier Discharges" *Applied Physics B* 46, 299–303, 1988.
Eliasson et al. "New Trends in High Intensity UV Generation" *EPA Newsletter* (32), 29–40, 1988.
Cotton, F.A. "Oxygen: Group Via(16)" *Advanced Inorganic Chemistry* 5th ed., 437–474, 1988.
Derwent Publications, Ltd., London, J6 2270665 (Konishiroku Photo KK), Nov. 25, 1987.
Abstract of patent, JP 62–215261 1987.
Database WPI, Derwent Publications Ltd., London, JP 62032082 (Mitsubishi Denki KK), Feb. 12, 1987.
Abstract of patent, JP 62–32082 1987.
Derwent Publications Ltd., London, J6 2007772 (Alps Electric KK.), Jan. 14, 1987.
Gross et al. "Laser direct–write metallization in thin palladium acetate films" *J. App. Phys.* 61 (4), 1628–1632, 1987.
Al–Ismail et al. "Some experimental results on thin polypropylene films loaded with finely–dispersed copper" *Journal of Materials Science,*415–418, 1987.
Baufay et al. "Optical self–regulation during laser–induced oxidation of copper" *J. Appl. Phys* 61 (9), 4640–4651, 1987.
Al–Ismail et al. "Some experimental results on thin polypropylene films loaded with finely–dispersed copper" *Journal of Materials Science* 415–418, 1987.
Gross et al. "Laser direct–write metallization in thin palladium acetate films" *J. App. Phys.* 61 (4), 1628–1632, 1987.
Derwent Publications Ltd., London, JA 0284478 (Sanyo Chem Ind Ltd.), Dec. 15, 1986.
Abstract of patent, JP 61251842 1986.
Database WPI, Derwent Publications Ltd., London, GB; SU, A, 1098210 (Kutulya L A) Jun. 23, 1986.
Abstract of patent, JP 61–97025 1986.
Abstract of patent, JP 61–87760 1986.
Derwent Publications Ltd., London, DL 0234731 (Karl Marx Univ. Leipzig), Apr. 9, 1986.
Derwent World Patents Index, SU 1219612 (AS USSR NON–AQ SOLN) Mar. 23, 1986.
Derwent Publications, Ltd., London, J6 1041381 (Osaka Prefecture), Feb. 27, 1986.
Dialog, JAPIO, JP 61–034057 (Ciba Geigy AG) Feb. 18, 1986.
Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201, 1986.
Jellinek, H.H.G. et al. "Evolution of H2O and CO2 During the Copper–Catalyzed Oxidation of Isotactic Polypropylene," *J. Polymer Sci.* 24 389–403, 1986.
Jellinek, H.H.G. et al. "Diffusion of Ca2+ Catalysts from Cu–Metal Polymer or Cu–Oxide/Polymer Interfaces into Isotactic Polypropylene" *J. Polymer Sci.* 24 503–510, 1986.
John J. Eisch and Ramiro Sanchez "Selective, Oxophilic Imination of Ketones with Bis (dichloroaluminum) Phenylimide" *J. Org. Chem.* 51 (10) 1848–1852, 1986.
Derwent Publications Ltd., London, J6 0226575 (Sumitomo Chem Ind Ltd.), Oct. 11, 1985.
Abstract of patent, JP 60–156761 1985.
Derwent Publications Ltd., London, J,A, 0011451 (Fugi Photo Film KK), Jan. 21, 1985.
Derwent Publications, Ltd., London J6 0011–449–A (Taoka Chemical KK) Jan. 21, 1985.
Roos, G. et al. "Textile applications of photocrosslinkable polymers" *Chemical Abstracts* 103 57 [No. 103:23690j ] 1985.
Derwent World Patents Index, EP 127574 (Ciba Geigy Ag), Dec. 15, 1984.
Derwent Publications Ltd., London, JP 0198187 (Canon KK), Nov. 9, 1984.
Derwent Publications Ltd., London, J,A, 0169883 (Ricoh KK), Sep. 25, 1984.
Derwent Publications Ltd., London, JA 0169883 (Ricoh KK), Sep. 25, 1984.
Derwent Publications Ltd., London, JA 0198187 (Canon KK), Sep. 11, 1984.
Derwent Publications Ltd., London, J,A, 0053563 (Dainippon Toryo KK), Mar. 28, 1984.
Derwent Publications Ltd., London, J,A, 0053562 (Dainippon Toryo KK), Mar. 28, 1984.
Abstract of Patent,JA 0053563 (Dainippon Toryo KK), Mar. 28, 1984.
Abstract of Patent,JA 0053562 (Dainippon Toryo KK), Mar. 28, 1984.
Derwent Publications Ltd., London, J,A, 0051961 (Dainippon Toryo KK), Mar. 26, 1984).
Abstract of Patent,JA 0051961 (Dainippon Toryo KK), Mar. 26, 1984.
Saenger, W. "Structural Aspects of Cyclodextrins and Their Inclusion Complexes" *Inclusion Compounds—Structural Aspects of Inclusion Compounds formed by Organic Host* 2, 231–259, 1984.
Szejtli "Industrial Applications of Cyclodextrins" *Inclusion Compounds: Physical Prop. & Applns* 3, 331–390 1984.
Kano et al. "Three–Component Complexes of Cyclodextrins. Exciplex Formation in Cyclodextrin Cavity," *J. Inclusion Phenomena* 2, pp. 737–746, 1984.
Suzuki et al. "Spectroscopic Investigation of Cyclodextrin Monomers, Derivatives, Polymers and Azo Dyes," *J. Inclusion Phenomena* 2, pp. 715–724, 1984.

Abstract of Patent, JA 0222164 (Ricoh KK), Dec. 23, 1983.
Abstract of patent, JP 58211426 (Sekisui Plastics KK), (Dec. 8, 1983).
Derwent Publications, Ltd., London, EP 0072775 (Ciba Geigy AG), Feb. 23, 1983.
van Beek, H.C.A "Light–Induced Colour Changes in Dyes and Materials" *Color Res. and Appl.* 8, 176–181, 1983.
Connors, K.A. "Application of a stoichiometric model of cyclodextrin complex formation" *Chemical Abstracts* 98, 598 [No. 98:53067g], 1983.
Abstract of Patent, EP 0065617 (IBM Corp.), Dec. 1, 1982.
Derwent Publications Ltd., London, J,A, 0187289 (Honshu Paper Mfg KK), Nov. 17, 1982.
Abstract of Patent, JA 0187289 (Honsho Paper Mfg KK), Nov. 17, 1982.
Abstract of Patent, JA 0185364 (Ricoh KK), Nov. 15, 1982.
Derwent Publications, Ltd., London J5 7139–146 (Showa Kako KK) Aug. 27, 1982.
Abstract of Patent, JA 0090069 (Canon KK), Jun. 4, 1982.
Derwent Publications, Ltd., London, JA 0061785 (Nippon Senka KK), Apr. 14, 1982.
Fischer, "Submicroscopic contact imaging with visible light by energy transfer" *Appl. Phys. Letter* 49(3), 1982.
Abstract of Patent, JA 0010659 (Canon KK), Jan. 2, 1982.
Abstract of Patent, JA 0010661 (Canon KK), Jan. 2, 1982.
Christen "Carbonylverbindungen: Aldehyde und Ketone," *Grundlagen der Organischen Chemie*, 255, 1982.
Derwent Publications Ltd., London, J,A, 0155263 (Canon KK), Dec. 1, 1981.
Abstract of Patent, JA 0155263 (Canon KK), Dec. 1, 1981.
Abstract of Patent, JA 0147861 (Canon KK), Nov. 17, 1981.
Derwent Publications Ltd., London, J,A, 0143273 (Canon KK), Nov. 7, 1981.
Abstract of Patent, JA 0143272 (Canon KK), Nov. 7, 1981.
Abstract of Patent, JA 0136861 (Canon KK), Oct. 26, 1981.
Abstract of Patent, JA 6133378 (Canon KK), Oct. 19, 1981.
Abstract of Patent, JA 6133377 (Canon KK), Oct. 19, 1981.
Abstract of Patent, JA 6093775 (Canon KK), Jul. 29, 1981.
Derwent Publications Ltd., London, J,A, 0008135 (Ricoh KK), Jan. 27, 1981.
Derwent Publications Ltd., London, J,A, 0004488 (Canon KK), Jan. 17, 1981.
Abstract of Patent, JA 0004488 (Canon KK), Jan. 17, 1981.
Kirk–Othmer "Metallic Coatings," *Encyclopedia of Chemical Technology*, 15, 241–274, 1981.
Komiyama et al. "One–Pot Preparation of 4–Hydroxychalcone β–Cyclodextrin as Catalyst,", *Makromol. Chem.* 2, 733–734, 1981.
Derwent Publications, Ltd., London CA 1086–719 (Sherwood Medical) Sep. 30, 1980.
Rosanske et al. "Stoichiometric Model of Cyclodextrin Complex Formation", *Journal of Pharmaceutical Sciences* (5), 69, 564–567, 1980.
Semple et al. "Synthesis of Functionalized Tetrahydrofurans," *Tetrahedron Letters* 81, pp. 4561–4564, 1980.
Kirk–Othmer "Film Deposition Techniques," *Encyclopedia of Chemical Technology*, 10, 247–283, 1980.
Derwent World Patents Index, Derwent Info. Ltd., JP 5418941 (Toyo Pulp KK), Dec. 15, 1979.
Derwent World Patents Index, JP 54117536 (Kawashima F) Sep. 12, 1979.
Derwent Publications Ltd., London, J,A, 0005422 (Fuji Photo Film KK), Jan. 16, 1979.
Drexhage et al. "Photo–bleachable dyes and processes", *Research Disclosure*, 85–87, 1979.

"Color imaging devices and color filter arrays using photo–bleachable dyes", *Research Disclosure*, 22–23, 1979.
Wolff, N.E., et al. "Electrophotography" *Kirk–Othmer Encyclopedia of Chemical Technology*, 8, 794–826, 1979.
Derwent Publications Ltd., London, J,A, 0012037 (Pentel KK), Jan. 29, 1977.
Abstract of Patent, JA 0012037 (Pentel KK), Jan. 29, 1977.
Jenkins, P.W. et al., "Photobleachable dye material" *Research Disclosure* 18 [No. 12932], 1975.
Lamberts, R.L. "Recording color grid patterns with lenticules", *Research Disclosure* 18–19 [No. 12923], 1975.
Karmanova, L.S. et al., "Light stabilizers of daytime fluorescent paints", *Chemical Abstracts* 82, 147 [No. 59971p], 1975.
Prokopovich, B. et al., "Selection of effective photoinducers for rapid hardening of polyester varnish PE–250", *Chemical Abstracts* 83, 131 [No. 81334a], 1975.
"Variable Contrast Printing System", *Research Disclosure* 19 [No. 12931], 1975.
Lakshman "Electronic Absorption Spectrum of Copper Formate Tetrahydrate", *Chemical Physics Letters* 31, (2), 331–334, 1975.
Derwent Publications, Ltd., London J4 9131–226 (TNational Cash Register C) Dec. 16, 1974.
Chang, I.F., et al., "Color Modulated Dye Ink Jet Printer", *IBM Technical Disclosure Bulletin*, 17(5), 1520–1521, 1974.
"Darocur 1173: Liquid Photoiniator for Ultraviolet Curing of Coatings", 1974.
Hosokawa et al. "Ascofuranone, an antibiotic from Ascochyta," Japan Kokai 73 91,278. (Nov. 28, 1973).
Abstract of patent, NL 7112489 (Dec. 27, 1971).
Gafney et al. "Photochemical Reactions of Copper (II)—1, 3–Diketonate Complexes",*Journal of the Americqal Chemical Society*, 1971.
Derwent Publications, Ltd., London SU 292698–S Jan. 15, 1971.
Derwent World Patents Index,CS 120380 (Kocourek, Jan) Oct. 15, 1966.
Rigdon, J.E. "In Search of Paper that Spies Can't Copy", *Wall Street Journal*, 1970.
Chatterjee,S. et al. "Photochemistry of Carbocyanine Alkyltriphenylborate Salts: Intra–Ion–Pair Electron Transfer and the Chemistry of Boranyl Radicals",*J. Am. Chem. Soc.* 112, 6329–6338.
"Assay—Physical and Chemical Analysis of Complexes", *AMAIZO*, 1993.
"Cyclodextrin" *AMAIZO*, 1993.
"Beta Cyclodextrin Polymer (BCDP)", *AMAIZO*, 1993.
"Chemically Modified Cyclodextrins", *AMAIZO* 1993.
"Cyclodextrin Complexation", *American Maize Products Co.*, 1993.
"Monomers" *Scientific Polymer Products Inc.*, no date.
Suppan, Paul "Quenching of Excited States" *Chemistry and Light*, 65–69, no date.
Yamaguchi, H. et al. "Supersensitization. Aromatic ketones as supersensitizers", *Chemical Abstracts* 53 107 (d), no date.
Stecher, H. "Ultraviolet–absorptive additives in adhesives, lacquers and plastics", *Chemical Abstracts* 53, 14579 (c), no date.
Maslennikov, A.S., "Coupling of diazonium salts with ketones", *Chemical Abstracts* 60 3128e, no date.
Derwent Publications Ltd., London, 4 9128022, no date.
Abstract of Patent, JP 405195450, no date.
Rose, Philip I. "Gelatin," *Encyclopedia of Chemical Technology*, 7, 488–513, no date.

Ultraviolet Spectrum of 1-phenyl-4-hydroxy-methyl-1-penten-3-one

PHOTOREACTOR COMPOSITION AND APPLICATIONS THEREFOR

CROSS-REFERENCE TO RELATED APPLICATION

This application is a continuation of U.S. patent application Ser. No. 08/649,755 filed on May 29, 1996, now abandoned, which is a continuation-in-part application of U.S. Ser. No. 08/625,737, filed Mar. 29, 1996, now abandoned, which is a continuation-in-part application of U.S. Ser. No. 08/537,593 filed Oct. 2, 1995, now abandoned, and is a continuation-in-part of U.S. patent application Ser. No. 08/463,188, filed Jun. 5, 1995, now U.S. Pat. No. 5,739,175, and a continuation-in-part application of U.S. Ser. No. 08/327,077, filed Oct. 21, 1994, now abandoned, which is a continuation-in-part application of U.S. Ser. No. 08/268,685, filed Jun. 30, 1994, now abandoned, all of which are herein incorporated by reference.

TECHNICAL FIELD

The present invention relates to a composition and method for generating a reactive species. The present invention more particularly relates to a composition and method for generating reactive species which can be used to polymerize or photocure polymerizable unsaturated material. In particular, the present invention provides a photoreactor that absorbs radiation at a wavelength that is particularly suited to exposure to lamps that emit at substantially the same wavelength.

BACKGROUND OF THE INVENTION

The present invention relates to a method of generating a reactive species. The present invention also relates to radiation-initiated polymerization and curing processes. For convenience, much of the discussion which follows centers on free radicals as a particularly desirable reactive species. Such discussion, however, is not to be construed as limiting either the spirit or scope of the present invention.

Polymers have served essential needs in society. For many years, these needs were filled by natural polymers. More recently, synthetic polymers have played an increasingly greater role, particularly since the beginning of the 20th century. Especially useful polymers are those prepared by an addition polymerization mechanism, i.e., free radical chain polymerization of unsaturated monomers, and include, by way of example only, coatings and adhesives. In fact, the majority of commercially significant processes is based on free-radical chemistry. That is, chain polymerization is initiated by a reactive species which often is a free radical. The source of the free radicals is termed an initiator or photoinitiator.

Improvements in free radical chain polymerization have focused both on the polymer being produced and the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by either of two pathways:

(1) the photoinitiator undergoes excitation by energy absorption with subsequent decomposition into one or more radicals; or (2) the photoinitiator undergoes excitation and the excited species interacts with a second compound (by either energy transfer or a redox reaction) to form free radicals from the latter and/or former compound(s).

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, commercially available radiation sources, such as medium and high pressure mercury and xenon lamps, emit over a wide wavelength range, thus producing individual emission bands of relatively low intensity. Most photoinitiators only absorb over a small portion of the emission spectra and, as a consequence, most of the lamps' radiation remains unused. In addition, most known photoinitiators have only moderate quantum yields (generally less than 0.4) at these wavelengths, indicating that the conversion of light radiation to radical formation can be more efficient.

Thus, there are continuing opportunities for improvements in free radical polymerization photoinitiators.

SUMMARY OF THE INVENTION

The present invention addresses some of the difficulties and problems discussed above by the discovery of an efficient composition and method for utilizing radiation. Hence, the present invention includes a composition and methods for generating a reactive species which includes providing one or more wavelength-specific sensitizers in association with one or more reactive species-generating photoinitiators and irradiating the resulting wavelength specific photoreactor composition. One of the main advantages of the wavelength specific photoreactor composition of the present invention is that it can be used to efficiently generate reactive species under extremely low energy lamps, such as excimer lamps, as compared to prior art lamps.

The association of one or more wavelength-specific sensitizers with one or more reactive species-generating photoinitiators results in a structure that is a wavelength specific photoreactor composition, that is referred to herein for convenience as a photoreactor. The present invention includes arylketoalkene wavelength-specific sensitizers. One major advantage of the wavelength specific photoreactor compositions is the use of arylketoalkene wavelength-specific sensitizers. The wavelength specific photoreactor compositions that contain the arylketoalkene wavelength-specific sensitizers efficiently absorb radiation at wavelengths between approximately 250 nm and 350 nm. Even more advantageous are the arylketoalkene sensitizers wherein the alkene group is located between the aryl and keto groups.

Another major advantage of the photoreactor compositions of the present invention is that, when combined with polymerizable material, they cause rapid curing times in comparison to the curing times of the prior art with relatively low output lamps. Yet another advantage of the present invention is that the multi-photoinitiator photoreactors of the present invention or the multi-wavelength specific sensitizer photoreactors have even faster curing times in comparison to the single-photoinitiator photoreactors of the present invention and/or are more sensitive than the single sensitizer photoreactors of the present invention.

The photoreactor compositions of the present invention also differ from the prior art in that the prior art sensitizers absorb a band width of radiation, whereas the sensitizer of the present invention absorbs a substantially single wavelength. The use of a wavelength specific photoreactor composition capable of absorbing a substantially single wavelength of radiation results in an efficient photoreactor upon exposure to a very narrow bandwidth of radiation or upon exposure to a single wavelength of radiation. The present method involves effectively tuning the energy-absorbing entity, referred to herein as a wavelength specific photoreactor composition, or photoreactor for convenience, to efficiently utilize an emitted band of radiation. The wavelength-specific sensitizer effectively absorbs photons and efficiently transfers the absorbed energy to a photoinitiator which, in turn, generates a reactive species. The wavelength-specific sensitizer is adapted to have an absorption peak generally corresponding to a maximum emission band of the radiation source.

The present invention includes various combinations of wavelength-specific sensitizers and photoinitiators. By varying the combination, one can effectively increase the number of photoinitiators per wavelength specific photoreactor composition or effectively increase the number of wavelength-specific sensitizers per photoreactive composition.

The present invention also includes a method of polymerizing an unsaturated monomer by exposing the unsaturated monomer to radiation in the presence of the efficacious wavelength specific photoreactor composition described above. When an unsaturated oligomer/monomer mixture is employed in place of the unsaturated monomer, curing is accomplished.

The present invention further includes a film and a method for producing a film, by drawing an admixture of unsaturated polymerizable material and the wavelength specific photoreactor composition of the present invention, into a film and irradiating the film with an amount of radiation sufficient to polymerize the composition. When the unsaturated polymerizable material is an unsaturated oligomer/monomer mixture, curing is accomplished. The admixture may be drawn into a film on a nonwoven web or on a fiber, thereby providing a polymer-coated nonwoven web or fiber, and a method for producing the same.

The film can be a film containing a dye or a pigment and can be used in the printing industry. The film with the dye or pigment therein is applied to a substrate such as paper and is then exposed to a source of electromagnetic radiation at the appropriate wavelength thereby causing the film to be cured. The use of the present invention in the printing industry has several advantages including increased printing speeds, lower energy consumption, and lower heat production.

The present invention also includes an adhesive composition comprising an unsaturated polymerizable material admixed with the wavelength specific photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition. When the unsaturated polymerizable material in the adhesive is an unsaturated oligomer/monomer mixture, the adhesive is irradiated to cure the composition.

DETAILED DESCRIPTION OF THE INVENTION

Figure 1:
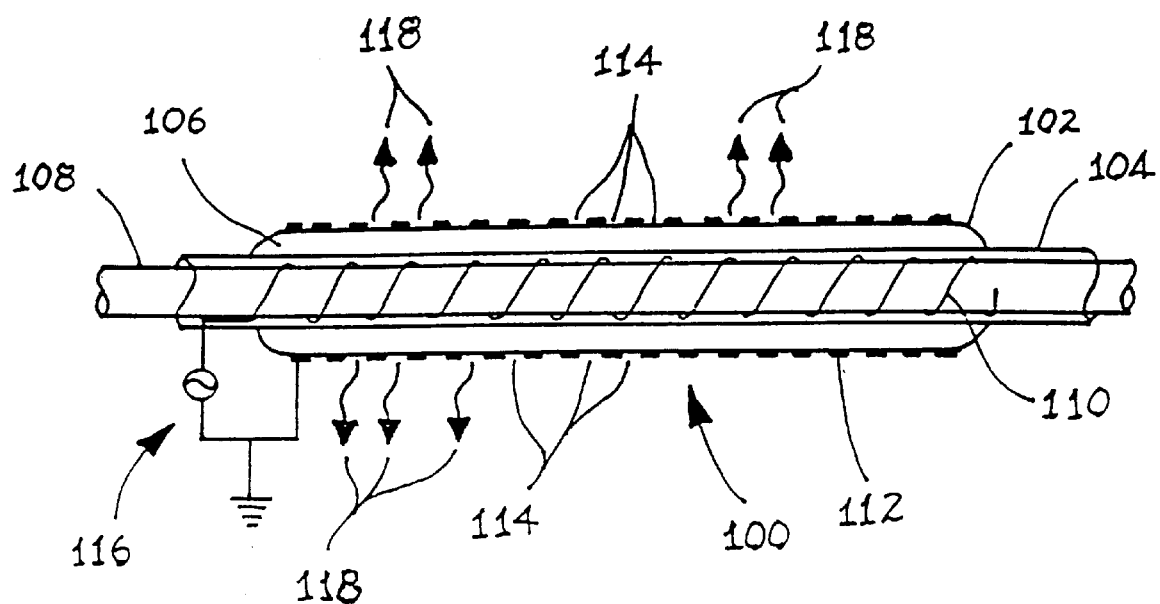
FIG. 1 is a diagrammatic representation of the excimer lamp employed in some of the examples.

The present invention is directed to the unexpected discovery of an efficient reactive species-generating composition and methods for utilizing the same. More particularly, the present invention includes a composition and method for generating a reactive species which includes providing one or more wavelength-specific sensitizers in association with one or more reactive species-generating photoinitiators and irradiating the wavelength-specific sensitizer. The association of one or more wavelength-specific sensitizers with one or more reactive species-generating photoinitiators results in a structure referred to herein as a wavelength specific photoreactor composition, or for convenience as a photoreactor composition.

The present invention also includes a method of polymerizing an unsaturated polymerizable material by exposing the unsaturated material to radiation in the presence of the efficacious wavelength specific photoreactor composition described above. Further, the present invention includes a film and a method for producing a film, by drawing an admixture of unsaturated polymerizable material and the wavelength specific photoreactor composition of the present invention, into a film and irradiating the film with an amount of radiation sufficient to polymerize the composition.

The film can be a film containing a dye or a pigment and can be used in the printing industry. The film with the dye or pigment therein is applied to a substrate such as paper and is then exposed to a source of electromagnetic radiation at the appropriate wavelength thereby causing the film to be cured. The use of the present invention in the printing industry has several advantages including increased printing speeds, lower energy consumption, and lower heat production.

Also, the present invention includes an adhesive composition comprising an unsaturated polymerizable material admixed with the wavelength specific photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition.

After the following definitions, the wavelength specific photoreactor composition of the present invention will be described in detail, followed by a detailed description of the method of generating reactive species, and the various representative applications of the method.

Definitions

The wavelength specific photoreactor composition of the present invention is one or more wavelength-specific sensitizers associated with one or more reactive species-generating photoinitiators. Accordingly, the term "wavelength specific photoreactor composition" is used herein to mean one or more wavelength-specific sensitizers or wavelength-specific sensitizer moieties associated with one or more reactive species-generating photoinitiators or reactive-species generating photoinitiator moieties. In an embodiment where the sensitizer(s) is admixed with the photoinitiator(s), the term "wavelength specific photoreactor composition" is used to mean the admixture. In the embodiment where the sensitizer(s) or sensitizer moiety (ies) are covalently bonded to the photoinitiator(s), or photoinitiator moiety (ies) the term "wavelength specific photoreactor composition" is used to mean the resultant molecule.

The term "single-photoinitiator photoreactor" is used to mean a wavelength specific photoreactor composition having one reactive species-generating photoinitiator or photoinitiator moiety therein. The term "multi-photoinitiator photoreactor" is used to mean a wavelength specific photoreactor composition having more than one reactive species-generating photoinitiator or photoinitiator moiety. Therefore, it follows that the term "double-photoinitiator photoreactor" is used to mean a wavelength specific photoreactor composition having two reactive species-generating photoinitiators or photoinitiator moieties.

The present invention also contemplates a wavelength specific photoreactor wherein there is a single reactive species-generating photoinitiator or photoinitiator moiety and multiple wavelength-specific sensitizers or sensitizer moieties. Accordingly, the term "double-sensitizer photoreactor" is used to mean a wavelength specific photoreactor composition having two wavelength-specific sensitizers or sensitizer moieties. Finally, the present invention includes wavelength specific photoreactor compositions with multiple wavelength specific sensitizers or sensitizer moiety and multiple reactive species-generating photoinitiators or photoinitiator moieties.

The term "associated" as used herein is meant to include any means which results in the wavelength-specific sensitizer(s) or sensitizer moiety (ies) and the reactive species-generating photoinitiator(s) or photoinitiator moiety (ies) being in sufficiently close proximity to each other to permit the transfer of energy absorbed by the sensitizer(s) or sensitizer moieties to the photoinitiator(s) or photoinitiator moiety (ies). For example, the wavelength-specific sensitizer(s) or sensitizer moiety (ies) and the reactive species-generating photoinitiator(s) may be bonded to each other or to a spacer molecule as described hereinafter by covalent, hydrogen, van der Waals, or ionic bonds. Alternatively, the sensitizer(s) and the photoinitiator(s) may be physically admixed.

The term "spacer molecule" is used herein to mean any molecule which aids in the bonding process. For example, a spacer molecule may assist in the bonding reaction by relieving steric hindrance. Alternatively, a spacer molecule may allow use of more reactive or more appropriate functional groups, depending upon the functional groups present in the sensitizer and photoinitiator moieties. It is contemplated that a spacer molecule may aid in the transfer of energy from the sensitizer moiety to the photoinitiator, moiety by either allowing a more favorable conformation or providing a more favorable energy transfer pathway.

The term "wavelength-specific sensitizer" or sensitizer moiety is used herein to mean that the sensitizer or sensitizer moiety is adapted to have an absorption wavelength band generally corresponding to an emission peak of the radiation. Either or both of the sensitizer or sensitizer moiety and the radiation may have more than one absorption wavelength band and emission peak, respectively. In the event both the sensitizer or sensitizer moiety and the radiation have more than one absorption wavelength band and emission peak, respectively, the general correspondence just described need not be limited to a single absorption wavelength band and a single emission peak.

The term "reactive species" is used herein to mean any chemically reactive species including, but not limited to, free-radicals, cations, anions, nitrenes, and carbenes. Illustrated below are examples of several of such species. Examples of carbenes include, for example, methylene or carbene, dichlorocarbene, diphenylcarbene, alkylcarbonylcarbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, primary, secondary, and tertiary alkyl carbocations, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, npropyl anion, isobutyl anion, and neopentyl anion; cycloalkyl anions, such as cyclopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diaryltitanocenes, iron arene complexes, manganese decacarbonyl, and methylcyclopentadienyl manganese tricarbonyl. Organometallic photoinitiators generally produce free radicals or cations.

The term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

The term "polymerization" is used herein to mean the combining, e.g. covalent bonding, of large numbers of smaller molecules, such as monomers, to form very large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a crosslinked polymer network. Thus, curing is the polymerization of unsaturated monomers or oligomers in the presence of crosslinking agents.

The terms "unsaturated monomer," "functional oligomer," and "crosslinking agent" are used herein with their usual meanings and are well understood by those having ordinary skill in the art. The singular form of each is intended to include both the singular and the plural, i.e., one or more of each respective material.

The term "unsaturated polymerizable material" is meant to include any unsaturated material capable of undergoing polymerization. The term encompasses unsaturated monomers, oligomers, and crosslinking agents. Again, the singular form of the term is intended to include both the singular and the plural.

The term "fiber" as used herein denotes a threadlike structure. The fibers used in the present invention may be any fibers known in the art. The term "nonwoven web" as used herein denotes a web-like matter comprised of one or more overlapping or interconnected fibers in a nonwoven manner. It is to be understood that any nonwoven fibers known in the art may be used in the present invention.

Wavelength Specific Photoreactor Composition

The present invention is directed to the unexpected discovery of an efficient reactive species-generating composition and methods for utilizing the same. More particularly, the present invention includes a composition and method for generating a reactive species which includes providing one or more wavelength-specific sensitizers or sensitizer moieties in association with one or more reactive species-generating photoinitiators and irradiating the wavelength-specific sensitizer or sensitizer moieties. The association of one or more wavelength-specific sensitizers with one or more reactive species-generating photoinitiators photoinitiator moieties results in a structure referred to herein as a wavelength specific photoreactor composition or, for simplicity, as a photoreactor composition.

A desirable photoreactor composition of the present invention is an arylketoalkene sensitizer moiety bonded to a photoinitiator, moiety wherein the alkene group is located between the aryl group and the keto group, having the following general formula:

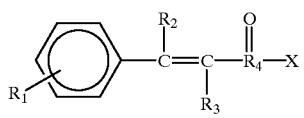

wherein X is a reactive-species generating photoinitiator, moiety and the remainder of the photoreactor is the wavelength-specific sensitizer; moiety wherein $R_1$ is hydrogen, an alkyl, alkenyl, cycloalkyl, heterocycloalkyl, aryl, heteroaryl group, or carbonyl group;

$R_2$ is hydrogen, alkyl, cycloalkyl, or a heterocycloalkyl group;

$R_3$ is hydrogen, alkyl, cycloalkyl, or a heterocycloalkyl group;

$R_4$ is a carbon or sulfur atom; and

X is one of the following photoinitiator moieties:

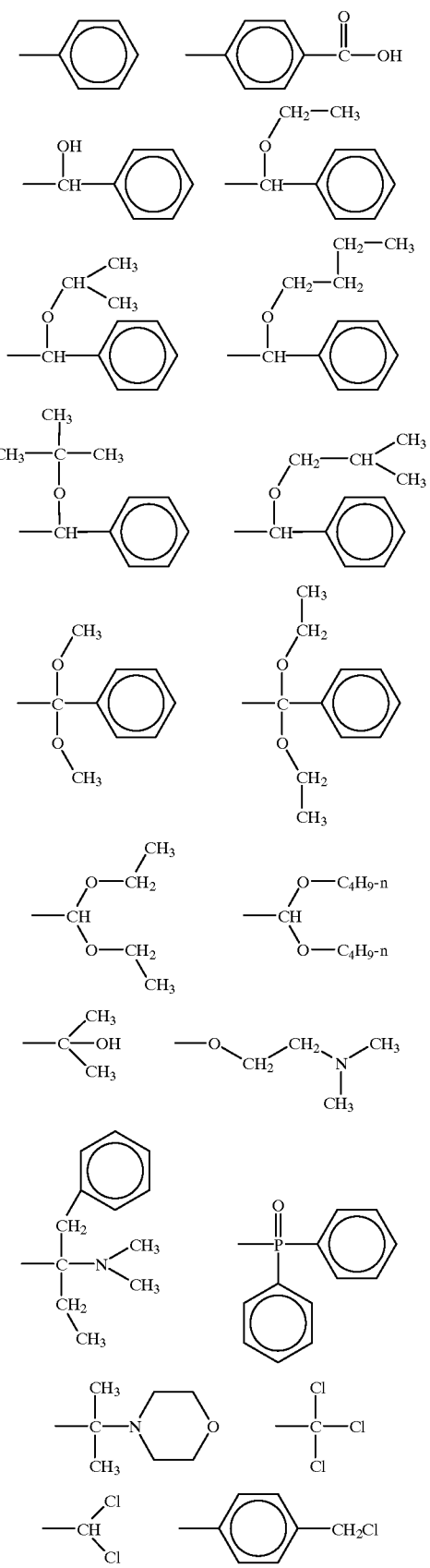

-continued

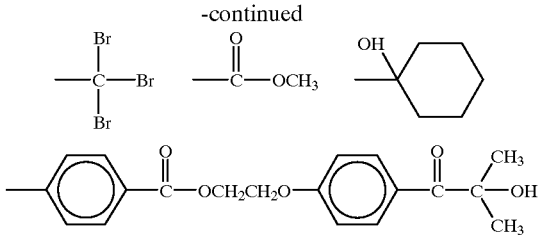

Additionally, X optionally may contain a spacer molecule covalently bonded to one of the above photoinitiator moieties, wherein the spacer is covalently bonded to the photoinitiator moieties and the sensitizer, and the spacer is located between the photoinitiator moiety and the sensitizer moiety.

Preferably, the above photoreactor is in the trans configuration with respect to the double bond. However, the photoreactor may be in the cis configuration across the double bond.

Desirably, $R_4$ is a carbon atom, so that the photoreactor composition has the following general formula:

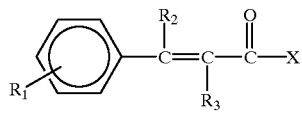

More desirably, $R_1$, $R_2$, and $R_3$ are hydrogen, and $R_4$ is a carbon atom, so that the photoreactor composition has the following general formula

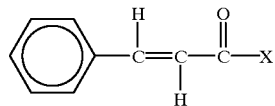

Even more desirably, the photoreactor of the present invention is 1-phenyl-4-hydroxy-4-methyl-1-penten-3-one having the following formula:

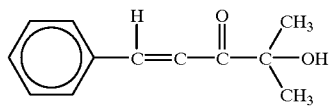

A method of synthesizing 1-phenyl-4-hydroxy-4-methyl-1-penten-3-one in a potassium hydroxide/ethanol/water solution at 20–25° C. is described in Example 19, and is summarized below:

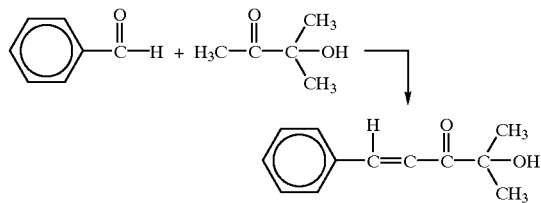

Additionally, 1-phenyl-4-hydroxy-4-methyl-1-penten-3-one may be synthesized in a sodium hydroxide/ethanol/water solution at 25–30° C. It is to be understood that the photoreactors of the present invention can be prepared by other methods known to one of ordinary skill in the chemical arts.

A method of photocuring using 1-phenyl-4-hydroxy-4-methyl-1-penten-3-one is described in Example 20. It is to be understood that the photoreactors of the present invention can be cured by other methods known in the art, but preferably will be cured with excimer lamps emitting the appropriate wavelength of radiation with respect to the sensitizer or sensitizer moiety present in the photoreactor. For example, it is desirable to utilize an excimer lamp that emits radiation having a wavelength of approximately 222 nm with the sensitizers (or sensitizer moiety) phthaloylglycine or 4-(4-hydroxyphenyl) butan-2-one. Similarly, it is desirable to utilize an excimer lamp that emits radiation having a wavelength of approximately 308 nm with the arylketoalkene sensitizers, (or sensitizer moieties) including those having the alkene group located between the aryl and the keto groups. It is also to be understood that the photoreactors of the present invention can be used to photocure any unsaturated polymerizable material.

The curing results obtained with 1-phenyl-4-hydroxy-4-methyl-1-penten-3-one, as described in Example 20, are unexpectedly efficient. Even with the most difficult compositions to cure, namely black inks, only 2% by weight of the photoreactor was needed, and only a 0.05 second flash of a 308 nm excimer lamp was needed to cure black ink.

Other desirable photoreactors of the present invention, wherein the alkene group is located between the aryl and keto group, including the following:

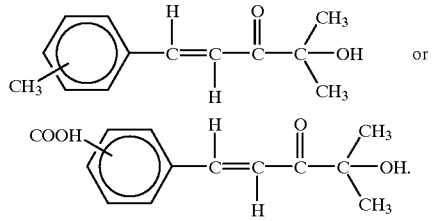

In another embodiment of the present invention, a desirable "wavelength-specific sensitizer" or sensitizer moiety is an arylketoalkene wavelength-specific sensitizer or sensitizer moiety having the following general formula:

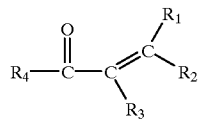

wherein $R_1$ is hydrogen, an alkyl, alkenyl, cycloalkyl, heterocycloalkyl, aryl or a heteroaryl group;

$R_2$ is hydrogen, alkyl, alkenyl, cycloalkyl, heterocycloalkyl, aryl or a heteroaryl group;

$R_3$ is hydrogen, alkyl, alkenyl, cycloalkyl, heterocycloalkyl, aryl or a heteroaryl group; and $R_4$ is an aryl, heteroaryl, or substituted aryl group.

A desirable sensitizer produced by the process of dehydrating a tertiary alcohol that is alpha to a carbonyl group on a sensitizer is represented in the following general formula:

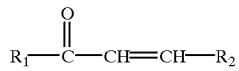

wherein when $R_1$ is an aryl group, $R_2$ is a hydrogen; alkyl; aryl; heterocyclic; or phenyl group, the phenyl group optionally being substituted with an alkyl, halo, amino, or thiol group; and wherein when $R_2$ is an aryl group, $R_1$ is a hydrogen; alkyl; aryl; heterocyclic; or phenyl group, the phenyl group optionally being substituted with an alkyl, halo, amino, or thiol group. Preferably, the alkene group is in the trans configuration. The wavelength-specific sensitizer of the present invention contains an aryl group, a carbonyl group, and a double bond (alkene group), in any order, such that resonance of the unshared electrons occurs.

In one embodiment, the arylketoalkene sensitizer is a chalcone having the following formula:

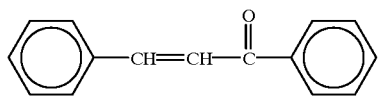

which efficiently absorbs radiation having a wavelength at about 308 nanometers, or is benzylideneacetone (4-phenyl-3-buten-2-one) having the following formula:

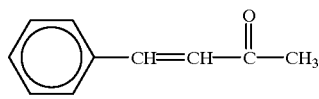

which efficiently absorbs radiation having a wavelength at about 280 nanometers. Desirably, the sensitizer of the present invention is in the trans configuration with respect to the double bond. However, the sensitizer may also be in the cis configuration across the double bond.

Although the above sensitizers are desirable, any sensitizer known in the art capable of absorbing photons having a substantially specific wavelength and transferring the absorbed energy to an associated reactive-species generating photoinitiator may be used in the present wavelength specific photoreactor compositions. As a practical matter, two classes of compounds are known to be useful as wavelength-specific sensitizers, namely, phthalic acid derivatives and phenyl-substituted aliphatic ketones. A particularly useful example of each class is phthaloylglycine and 4-(4-hydroxyphenyl)butan-2-one, respectively, both of which absorb radiation having a wavelength of approximately 222 nm. Therefore, another desirable sensitizer is phthaloylglycine having the following formula:

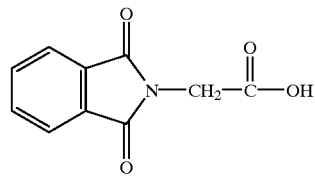

or 4-(4-hydroxyphenyl)butan-2-one having the following formula

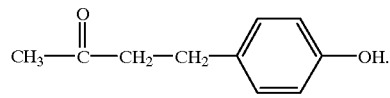

As stated above, the wavelength-specific sensitizer of the present invention, in the form of a wavelength-specific sensitizer moiety, may optionally be covalently bonded to one or more reactive species-generating photoinitiators. In that embodiment, the aryl group of a wavelength-specific sensitizer moiety of the present invention can contain a group including, but not limited to, a carboxylic acid group, an aldehyde group, an amino group, a haloalkyl group, a hydroxyl group, or a thioalkyl group attached thereto to allow the arylketoalkene to be covalently bonded to the other molecule. Accordingly, a desired arylketoalkene stabilizing compound includes the following:

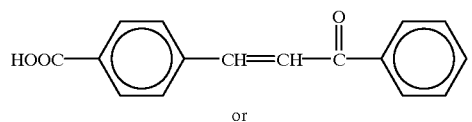

or

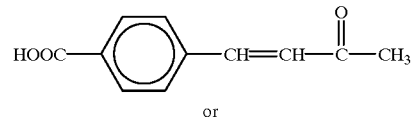

or

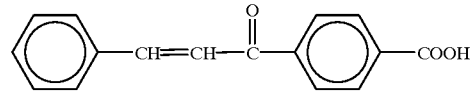

or

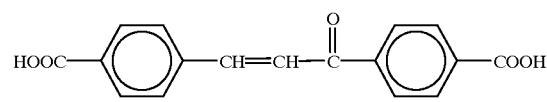

Although it is preferred that the group attached to the aryl group is para to the remainder of the stabilizer molecule, the group may also be ortho or meta to the remainder of the molecule. Note that the di-carboxylic acid substituted chalcone type compound shown above can be covalently bonded to two photoinitiator moieties one photoinitiator moiety on each aryl group substituted with a carboxylic acid group, thereby producing a double-photoinitiator moiety photoreactor.

In the embodiment where the sensitizer is phthaloylglycine, and two photoinitiator moiety are covalently bonded thereto, the phenyl group will contain a group including, but not limited to, a carboxylic acid group, an aldehyde group, an amino group, a haloalkyl group, a hydroxyl group, or a thioalkyl group attached thereto to allow the phthaloylglycine to be covalently bonded to one photoinitiator moiety. Of course, the carboxylic acid group in the phthaloylglycine provides the second location for covalently bonding to the second photoinitiator moiety.

Any reactive species-generating photoinitiator or photoinitiator moiety may be used which generates the desired reactive species. With regard to the free radical-generating photoinitiators, these photoinitiators or photoinitiator moieties may be any of the photoinitiators photoinitiators moieties known to those having ordinary skill in the art. The largest group of photoinitiators are carbonyl compounds, such as ketones, especially α-aromatic ketones. Examples of α-aromatic ketone photoinitiators include, by way of illustration only, benzophenones; xanthones and thioxanthones; α-ketocoumarins; benzils; α-alkoxydeoxybenzoins; benzil ketals or α, α-dialkoxydeoxybenzoins; enzoyldialkylphosphonates; acetophenones, such as α-hydroxycyclohexyl phenyl ketone, α,α-dimethyl-α-hydroxyacetophenone, α, α-dimethyl-α-morpholino-4-methylthio-α-acetophenone, α-ethyl-α-benzyl-α-dimethylaminoacetophenone, α-ethyl-α-benzyl-α-dimethylamino-4-morpholinoacetophenone, α-ethyl-α-benzyl-α-dimethylamino-3,4dimethoxy-acetophenone,α-ethyl-α-benzyl-α-dimethylamino-4-methoxyacetophenone, α-ethyl-α-benzyl-α-dimethylamino-4-dimethylaminoacetophenone, α-ethyl-α-benzyl-α-dimethylamino-4-methylacetophenone, α-ethyl-α-(2-propenyl)-α-dimethylamino-4-morpholino-acetophenone,α,α-bis(2-propenyl)-α-dimethylamino-4-morpholinoacetophenone, α-methyl-α-benzyl-α-dimethylamino-4-morpholinoacetophenone, and α-methyl-α-(2-propenyl)-α-dimethylamino-4-morpholinoacetophenone; α,α-dialkoxyaceto-phenones; α-hydroxyalkylphenones; O-acyl α-oximino ketones; acylphosphine oxides; fluorenones, such as fluorenone, 2-t-butylperoxycarbonyl-9-fluorenone, 4-t-butylperoxyvarbonyl-nitro-9-fluorenone, and 2,7-di-t-butylperoxycarbonyl-9-fluorenone; and α- and β-naphthyl carbonyl compounds.

Examples of the above photoinitiators include, but are not limited to the following: benzoin; benzoin ethyl ether; benzoin isopropyl ether; benzoin n-butyl ether; benzoin butyl ether; benzoin iso-butyl ether; benzildimethyl ketal; 2,2-diethoxy-1,2-diphenylethanone; α,α-diethoxyacetophenone; α,α-di( n-butoxy)acetophenone; 2-hydroxy-2-methyl-1-phenyl-propan-1-one; 1-(4-isopropylphenyl)-2-hydroxy-2-methyl-propan-1-one; 1-(4-(2-hydroxyethoxy)pheny)-2-hydroxy-2-methyl-propan-1-one; 2-isopropyl thioxantone; 1-(4-dimethyl-aminophenyl) ethanone; 2-methyl-1-(4-(methylthio)phenyl)-2-morpholino-propan-1-one; 2-benzyl-2-dimethylamino-1-(4-morpholinophenyl)-butan-1-one; 3,6-bis(2-methyl-2-morpholino-propanonyl)-9-butyl-carbazole; 2,4,6-trimethylbenzoyl-diphenyl-phosphine oxide; 2,2,2-trichloro-1-(4-(1,1-dimethylethyl)phenyl)-ethanone; 2,2-dichloro-1-(4-phenoxyphenyl)-ethanone; 4,4'-bis (chloromethyl)-benzophenone; phenyl-tribromomethyl-sulphone; and methyl α-oxo benzeneacetate.

Other free radical generating photoinitiators include, by way of illustration, triarylsilyl peroxides, such as triarylsilyl t-butyl peroxides; acylsilanes; and some organometallic compounds. The free radical-generating initiator desirably will be an acetophenone. More desirably, the photoinitiator will be IRGACURE®-2959 (1-[4-(2-hydroxyethoxy) phenyl]-2-hydroxy-2-methylpropan-1-one or 2-hydroxy-4'-(2-hydroxyethoxy)-2-methylpropiophenone) having the following structure

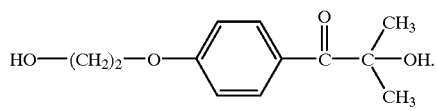

Another desirable photoinitiator is IRGACURE® 184 (1-hydroxycyclohexane phenyl ketone), having the following formula:

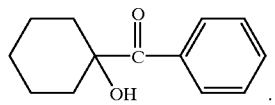

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

In the embodiments where one or more wavelength-specific sensitizers or sensitizer moieties are bound to one or more reactive species-generating photoinitiators, or photoiniators moieties any suitable method that is known in the art may be used to bond the sensitizer moiety (ies) to the or photoiniator moiety (ies). The choice of such method will depend on the functional groups present in the sensitizer and photoiniator moieties and is readily made by those having ordinary skill in the art. Such bonding may be accomplished by means of functional groups already present in the molecules to be bonded, by converting one or more functional groups to other functional groups, by attaching functional groups to the molecules, or through one or more spacer molecules.

Examples 1–3, and 30 herein describe methods of preparing the arylketoalkene sensitizer of the present invention, and covalently bonding it to a photoinitiator, moiety namely IRGACURE® -2959. Examples 1 and 30 both describe a method of synthesizing the following wavelength-specific sensitizer:

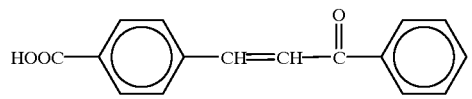

The method in Example 30 is a desired method of synthesizing the above wavelength-specific sensitizer. It is to be understood that other methods known in the art may be used to synthesize the above wavelength-specific sensitizer.

The reaction described in Example 3 may be used on any arylketoalkene sensitizer of the present invention having a carboxylic acid functional group on $R_1$ or $R_2$, whichever is the aryl group. This reaction of any arylketoalkene sensitizer is represented by the formula below, wherein $R_3$ represents the remainder of the arylketoalkene sensitizer of the present invention, and wherein the carboxylic acid group is attached to $R_1$ and/or $R_2$:

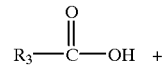

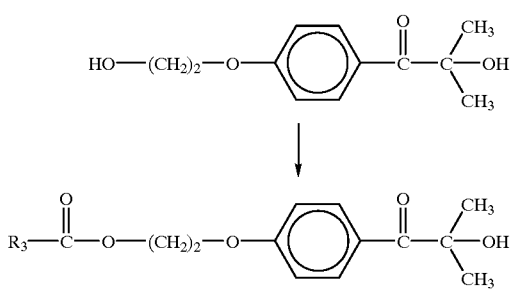

In the embodiment where both $R_1$ and $R_2$ are phenyl groups, if a carboxylic acid group is attached to only one of the phenyl groups, a single-photoinitiator photoreactor is produced. In the embodiment where both $R_1$ and $R_2$ are phenyl groups, and a carboxylic acid group is attached to both phenyl groups, a double-photoinitiator photoreactor is produced.

A wavelength specific photoreactor composition of the present invention is represented by the following formula:

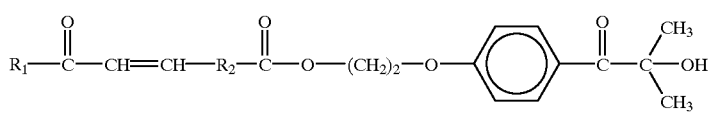

Another wavelength specific photoreactor composition of the present invention is represented by the following formulas:

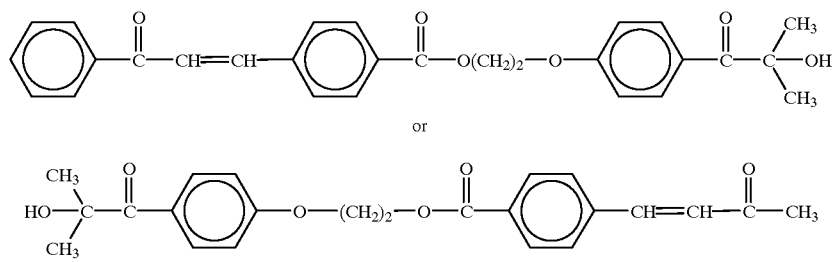

Another wavelength specific photoreactor composition that is considered part of the present invention is the compound represented by the following formula:

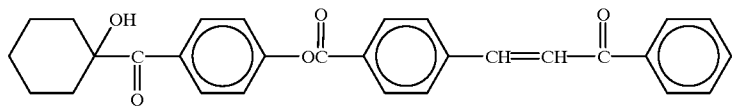

Synthesis of this wavelength specific photoinitiator composition is described in Examples 9 through 12 herein.

Another wavelength specific photoreactor composition of the present invention is a "double-photoinitiator photoreactor" or a "double-sensitizer photoreactor". These compositions, for example the double-photoinitiator or the double-sensitizer photoreactor compositions, are generally more sensitive to the electromagnetic radiation and are useful in situations were increased sensitivity is required. Although not wanting to be limited by the following, it is theorized that the double-photoinitiator photoreactor is more sensitive as more reactive species are generated per photon absorbed than if the photoreactor contained only one reactive-species generating photoinitiator moiety. Also, although not wanting to be limited by the following, it is theorized that the double-sensitizer photoreactor is more likely to absorb a photon of radiation than a single-sensitizer photoreactor as the double-sensitizer photoreactor contains two sensitizer moieties, and therefore in situations where there is little light present, such a double-sensitizer photoreactor is more likely to absorb radiation than a photoreactor having only one sensitizer moieties.

One example of a double-photoinitiator wavelength specific photoreactor composition of the present invention is represented by the following formula:

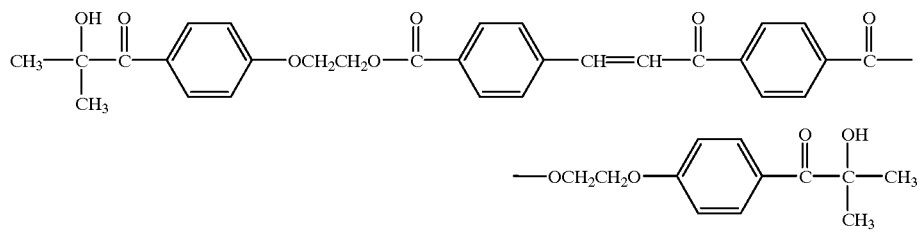

Example 6 herein describes a method of preparing a double carboxylic acid substituted chalcone and then the method of preparing the above double-photoinitiator photoreactor. The reaction for preparing the double-photoinitiator photoreactor described in Example 6 may be used on any sensitizer of the present invention having two carboxylic acid functional groups on each end of the sensitizer.

The method of preparing the double carboxylic acid substituted chalcone is illustrated as follows:

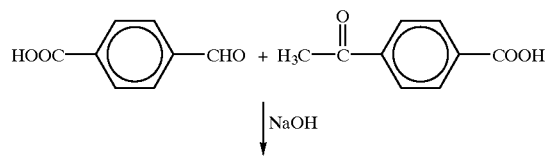

-continued

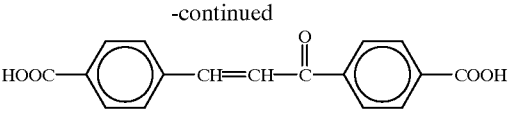

It is to be understood that other methods known to those of ordinary skill in the chemical arts may be used to prepare the above double carboxylic acid substituted chalcone, or any other double carboxylic acid substituted sensitizer. It is also to be understood that other methods known in the art may be used to prepare-sensitizers that are substituted with one or more of the other functional groups listed above. It is further to be understood that the functional groups on a sensitizer may be the same or they may be different.

The method of preparing the double-photoinitiator photoreactor from the above double carboxylic acid substituted chalcone is illustrated as follows:

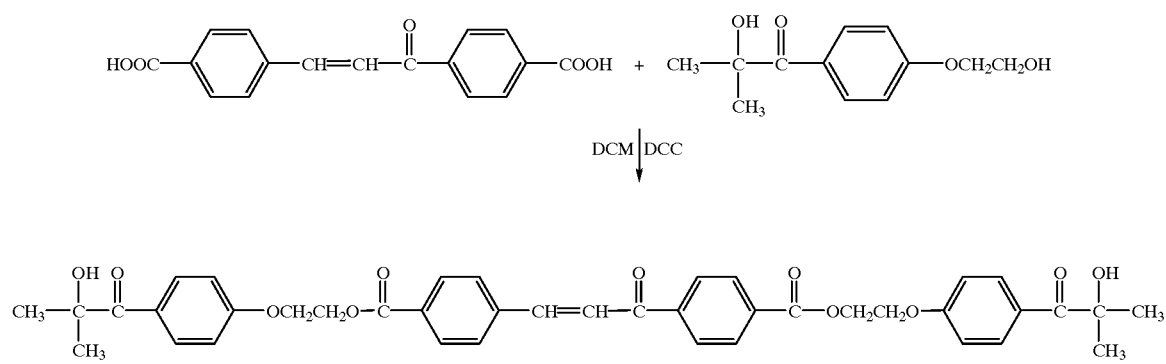

The above illustrated double-photoinitiator photoreactor can be referred to as a "chalcone double-photoinitiator photoreactor", in contrast to other double-photoinitiators within the present invention as will be further discussed below.

Another wavelength specific photoreactor composition of the present invention is a "double-wavelength specific sensitizer photoreactor". One example of this double-wavelength specific photoreactor composition is represented by the following formula:

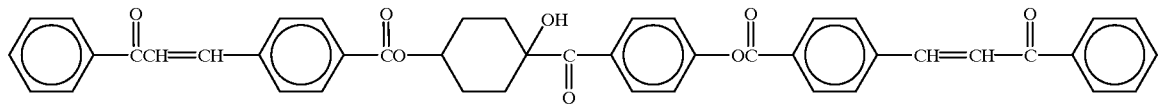

Synthesis of this wavelength specific photoinitiator composition is shown in Examples 13 through 17 herein. Another double-wavelength specific sensitizer photoreactor of the present invention comprises the compound represented by the following formula:

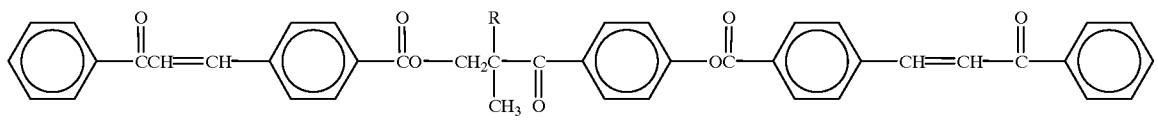

It is to be understood that "R" in the above formula is preferably a hydroxyl group, but it can be an alkyl group including, but not limited to, a methyl, ethyl, propyl or butyl group. The important feature of the reactive species generating portion of the molecule is the tertiary carbon atom that is in the alpha position to the carboxyl group.

It is to be understood that the above reactions are merely one method of binding a one or more wavelength sensitizer moieties to one or more photoiniator moieties, and that other methods known in the art may be used.

As discussed above, sensitizers other than the arylketoalkene sensitizers above may be in the wavelength specific photoreactor compositions of the present invention. For example, the sensitizer moiety phthaloylglycine may be covalently bonded to one or two photoiniator moieties as is illustrated below, wherein the top wavelength specific photoreactor composition is one IRGACURE-2959 photoinitiator moiety covalently bonded to phthaloylglycine; the second wavelength specific photoreactor composition is two IRGACURE®-2959 photoinitiators covalently bonded to phthaloylglycine; and the third wavelength specific photoreactor composition is two phthaloylglycine sensitizer moieties covalently bonded to one IRGACURE-2959 photoiniator moieties. The structures are shown as follows: 2-[p-(2-methyllactoyl)phenoxy]ethyl 1,3-dioxo-2-isoindolineacetate, having the following structure:

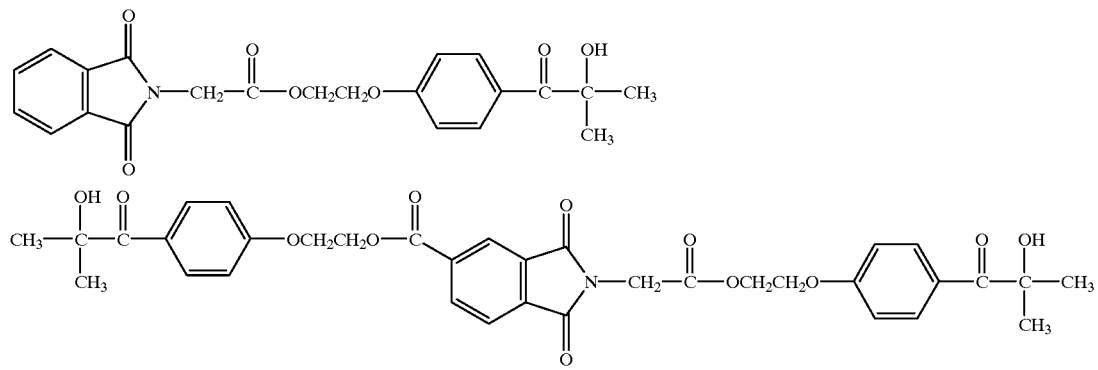

1,3-dioxo-2-isoindolineacetic acid diester with 2-hydroxy-4'-(2-hydroxyethoxy)-2-methylpropiophenone, having the following structure:

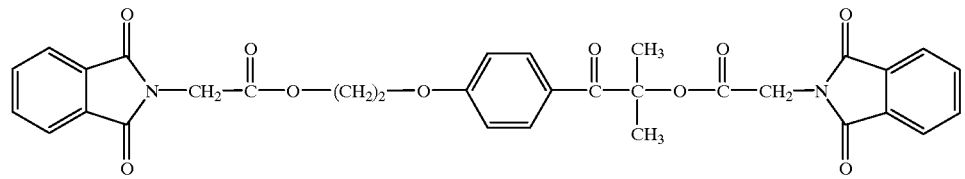

Similarly, the sensitizer moiety 4-(4-hydroxyphenyl) butan-2-one may be covalently bonded to one or two photoiniator moieties. As illustrated below, the first photoreactor is one 4-(4-hydroxyphenyl) butan-2-one sensitizer moiety covalently bonded to one IRGACURE®-2959 photoinitiator, moiety and the second photoreactor is one 4-(4-hydroxyphenyl) butan-2-one sensitizer moiety covalently bonded to one IRGACURE® 184 photoinitiator. The structures are shown as follows: 2-hydroxy-2-methyl-4'-[2-[p-(3-oxobutyl)phenoxy]ethoxy]propio-phenone having the following structure:

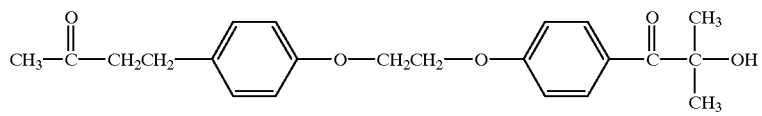

4-[p-[(4-benzoylcyclohexyl)oxy]phenyl]-2-butanone, having the following structure:

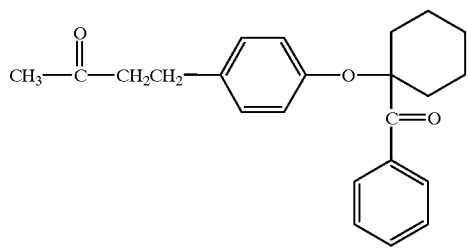

The synthesis of the above photoreactors containing either phthaloylglycine or 4-(4-hydroxyphenyl) butan-2-one as the wavelength-specific sensitizer moiety is described in Examples 21 through 24. Examples 25 through 29 describe methods of curing the above photoreactor compositions and their respective curing results.

As noted earlier, the wavelength-specific sensitizer or sensitizer moiety is adapted to have an absorption wavelength band generally corresponding to an emission peak of the radiation. In addition, the wavelength-specific sensitizer or sentizer moiety will have a high intensity of absorption. For example, the wavelength-specific sensitizer or sentizer moiety may have a molar extinction coefficient greater than about 2,000 liters per mole per cm (1 mole$^{-1}$cm$^{-1}$) at an absorption maximum. As another example, the wavelength-specific sensitizer may have a molar extinction coefficient (absorptivity) greater than about 5,000 l mole$^{-1}$cm$^{-1}$. As another example, the wavelength-specific sensitizer or sensitizer moiety may have a molar extinction coefficient (absorptivity) greater than about 10,000 l mole$^{-1}$cm$^{-1}$. As a further example, the wavelength-specific sensitizer or sensitizer moiety will have a molar extinction coefficient greater than about 20,000 l mole$^{-1}$ cm$^{-1}$.

The absorption characteristics of the wavelength-specific sensitizer or sensitizer moiety are not limited to a single wavelength band. Many compounds exhibit more than one absorption wavelength band. Consequently, a wavelength-specific sensitizer or sensitizer moiety may be adapted to absorb two or more wavelength bands of radiation. Alternatively, two or more wavelength-specific sensitizers or sensitizer moiety may be associated with a reactive species-generating photoinitiator or photoinitiator moiety. Such two or more wavelength-specific sensitizers or sensitizer moieties may absorb the same wavelength band or they may absorb two or more different wavelength bands of radiation.

Method of Generating a Reactive Species and Applications Therefor

The method of the present invention involves generating a reactive species by exposing a wavelength specific photoreactor composition to radiation in which the wavelength specific photoreactor composition includes a wavelength-specific sensitizer or sensitizer moiety associated with one or more reactive species-generating photoinitiators or photoinitiator moieties. In other words, the method involves providing a wavelength-specific sensitizer or sensitizer moiety in association with one or more reactive species-generating photoinitiators or photoinitiators moieties and irradiating the wavelength-specific sensitizer or sensitizer moiety.

As stated above, the term "quantum yield" is used herein to indicate the efficiency of a photochemical process. More particularly, quantum yield is a measure of the probability that a particular molecule will absorb a quantum of light during its interaction with a photon. The term expresses the number of photochemical events per photon absorbed. Thus, quantum yields may vary from zero (no absorption) to 1.

The sensitizer or sensitizer moiety absorbs photons having a specific wavelength and transfers the absorbed energy to an associated photoinitiator or photoinitiator moiety which, in turn, generates a reactive species. However, the efficiency with which a reactive species is generated is significantly greater than that experienced with the reactive species-generating photoinitiator alone. For example, the wavelength specific photoreactor composition desirably will have a quantum yield greater than about 0.5. More desirably, the quantum yield of the wavelength specific photoreactor composition will be greater than about 0.6. Even more desirably, the quantum yield of the wavelength specific photoreactor composition will be greater than about 0.7. Still more desirably, the quantum yield of the wavelength specific photoreactor composition will be greater than about 0.8, with the most desirable quantum yield being greater than about 0.9.

Exposing the wavelength specific photoreactor composition of the present invention to radiation results in the generation of one or more reactive species. Thus, the wavelength specific photoreactor composition may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene, propylene, vinyl chloride, isobutylene, styrene, isoprene, acrylonitrile, acrylic acid, methacylic acid, ethyl acrylate, methyl methacrylate, vinyl acrylate, allyl methacrylate, tripropylene glycol diacrylate, trimethylol propane ethoxylate acrylate, epoxy acrylates, such as the reaction product of a bisphenol A epoxide with acrylic acid; polyester acrylates, such as the reaction product of acrylic acid with an adipic acid/ hexanediol-based polyester, urethane acrylates, such as the reaction product of hydroxypropyl acrylate with diphenylmethane-4,4'-diisocyanate, and polybutadiene diacrylate oligomer.

Accordingly, the present invention also comprehends a method of polymerizing an unsaturated monomer by exposing the unsaturated monomer to radiation in the presence of the efficacious wavelength specific photoreactor composition described above. When an unsaturated oligomer/monomer mixture is employed in place of the unsaturated monomer, curing is accomplished. It is to be understood that the polymerizable material admixed with the wavelength specific photoreactor composition of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of wavelength specific photoreactor composition, the identity and amount of the polymerizable material, the intensity and wavelength of the radiation, and the duration of exposure to the radiation.

The present invention further includes a film and a method for producing a film, by drawing an admixture of unsaturated polymerizable material and the wavelength specific photoreactor composition of the present invention, into a film and irradiating the film with an amount of radiation sufficient to polymerize the composition. When the unsaturated polymerizable material is an unsaturated oligomer/monomer mixture, curing is accomplished. Any film.thickness may be produced, as per the thickness of the admixture formed, so long as the admixture sufficiently polymerizes upon exposure to radiation. The admixture may be drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of wavelength specific photoreactor composition, the identity and amount of the polymerizable material, the thickness of the admixture, the intensity and wavelength of the radiation, and duration of exposure to the radiation.

The present invention also includes an adhesive composition comprising an unsaturated polymerizable material admixed with the wavelength specific photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of wavelength specific photoreactor composition, the identity and amount of the polymerizable material, the thickness of the admixture, the identity and thickness of the layer, the intensity and wavelength of the radiation, and the duration of exposure to the radiation.

The radiation to which the wavelength specific photoreactor composition is exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers.

Desirably, when the reactive species-generating photoinitiator or photoinitiator moiety is an organic compound, or moiety the radiation will be ultraviolet radiation having a wavelength of from about 4 to about 400 nanometers. More desirably, the radiation will have a wavelength of from about 100 to about 375 nanometers, and even more desirably will have a wavelength of from 200 to about 370 nanometers. For example, the radiation may have a wavelength of from about 222 to about 308 nanometers. The radiation desirably will be incoherent, pulsed ultraviolet radiation from a dielectric barrier discharge excimer lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent dischargers the generation of ultraviolet and vacuum ultraviolet excimer radiation." Pure & Appi. Chem., 62, No. 9, pp. 16671674 (1990); and E. Eliasson and U. Kogelschatz, "UV Excimer Radiation from Dielectric- Barrier Discharges." Appl. Phys. B. 46, pp. 299–303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

As a result of the arylketoalkene wavelength-specific sensitizer, or sensitizer moiety including the sensitizer or sensitizer moiety having the alkene group located between the aryl and keto group, of the present invention absorbing radiation in the range of about 250 to about 350 nanometers, and more particularly at about 270 to 320 nanometers, the wavelength specific photoreactor composition of the present invention will generate one or more reactive species upon exposure to sunlight. Accordingly, this wavelength specific photoreactor composition of the present invention provides a method for the generation of reactive species that does not require the presence of a special light source.

This wavelength specific photoreactor composition of the present invention having the arylketoalkene sensitizer, or sensitizer moiety including the sensitizer or sensitizer moiety having the alkene group located between the aryl and keto group, enables the production of adhesive and coating compositions that consumers can apply to a desired object and polymerize or cure upon exposure to sunlight. This wavelength specific photoreactor composition also enables numerous industry applications wherein unsaturated polymerizable materials may be polymerized merely upon exposure to sunlight. Therefore, depending upon how the wavelength specific photoreactor composition is designed, the wavelength specific photoreactor composition of the present invention having the arylketoalkene sensitizer, or sensitizer moiety including the sensitizer or sensitizer moiety having the alkene group located between the aryl and keto group, can eliminate the cost of purchasing and maintaining light sources in numerous industries wherein such light sources are necessary without the wavelength specific photoreactor composition of the present invention.

The wavelength specific photoreactor compositions of the present invention also differ from the prior art in that the prior art sensitizers absorb a wide bandwidth of radiation. In fact, the prior art photoinitiators are designed to absorb as much radiation as possible over as wide a range as possible thereby increasing the efficiency of the photoinitiators when exposed to ordinary light. whereas the sensitizer of the present invention absorbs a single wavelength of radiation. The use of a wavelength specific photoreactor composition capable of absorbing at a substantially single wavelength of radiation results in an extremely efficient photoreactor upon exposure to a very narrow bandwidth of radiation or upon exposure to a single wavelength of radiation.

As shown in the Examples below, the superiority of the wavelength specific photoreactor compositions of the present invention over known photoinitiators is clear, even when the radiation is not the essentially monochromatic emission. The effective tuning of the wavelength specific photoreactor composition for a specific wavelength band permits the wavelength specific photoreactor composition to more efficiently utilize the target radiation in the emission spectrum of the radiating source corresponding to the "tuned" wavelength band, even though the intensity of such radiation may be much lower than, for example, radiation from a narrow band emitter, such as an excimer lamp. In other words, the effectiveness of the wavelength specific photoreactor composition of the present invention is not necessarily dependent upon the availability or use of a narrow wavelength band radiation source.

Also, as shown in Example 4, the single-photoinitiator photoreactor of the present invention is exceptionally efficient. In Example 4, a mixture of GENOMER® 1500B with a concentration of only about 0.5% of the single-photoinitiator photoreactor produced in Example 3 is totally cured upon exposure to the excimer lamp. The concentration of wavelength specific photoreactor composition used in Example 4 is substantially lower than the amounts normally used in the prior art. Typical concentrations of conventional photoreactors or photoinitiators in the prior art are between approximately 2% to 20% by weight.

Further, as shown in Example 7, the multi-photoinitiator photoreactors of the present invention are even more efficient than the single-photoinitiator photoreactors of the present invention. More particularly, Table 2 summarizes the curing times for a pigmented polymerizable formulation, wherein either a commercial photoinitiator product, the wavelength specific photoreactor composition produced in Example 3 or the wavelength specific photoreactor composition produced in Example 6 is admixed therein. The wavelength specific photoreactor composition produced in Example 6 had the shortest curing time, namely, 0.06 seconds. The wavelength specific photoreactor composition produced in Example 3 had a curing time of 0.10, and the commercial photoinitiator had a cure time that is 50 times greater than the wavelength specific photoreactor composition of Example 6, namely 3.0 seconds.

Accordingly, a major advantage of the wavelength specific photoreactor compositions of the present invention is that they have rapid curing times in comparison to the curing times of the prior art. Another advantage of the of the present invention is that the multi-photoinitiator photoreactors of the present invention have even faster curing times in comparison to the single-photoinitiator photoreactors of the present invention. Yet another advantage of the present invention is that the multi-sensitizer photoreactors and the multi-photoinitiator photoreactors of the present invention are highly sensitive photoreactors and are beneficially used in situations having lower light levels.

The present invention is further described by the examples which follow. Such examples, however, are not to be construed as limiting in any way either the spirit or the scope of the present invention. In the examples, all parts are by weight, unless stated otherwise.

Example 1

This example describes a method of synthesizing the following wavelength-specific sensitizer:

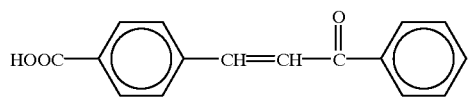

The wavelength-specific sensitizer is produced as summarized below:

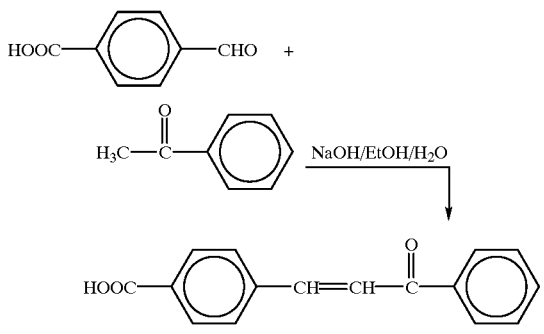

To a 250 ml round bottom flask fitted with a magnetic stir bar, and a condenser, is added 10.8 g (0.27 mole) sodium hydroxide (Aldrich), 98 g water and 50 g ethanol. The solution is stirred while being cooled to room temperature in an ice bath. To the stirred solution is added 25.8 g (0.21 mole) acetophenone (Aldrich) and then 32.2 g (0.21 mole) 4-carboxybenzaldehyde (Aldrich). The reaction mixture is stirred at room temperature for approximately 8 hours. The reaction mixture temperature is checked in order to prevent it from exceeding 30° C. Next, dilute HCl is added to bring the mixture to neutral pH as indicated by universal pH indicator paper. The white/yellow precipitate is filtered using a Buchner funnel to yield 40.0 g (75%) after drying on a rotary pump for four hours. The product is used below without further purification.

The resulting reaction product had the following physical parameters: Mass. Spec. m/e (m$^+$) 252, 207, 179, 157, 105, 77, 51.

The ultraviolet radiation spectrum of the product had an extinction coefficient of about 24,000 at about 304 nanometers, and $\lambda_{mas}$ is at 308 nanometers.

Example 2

This example describes a method of making the following wavelength-selective sensitizer, namely 4-[4'-carboxy phenyl]-3-buten-2-one:

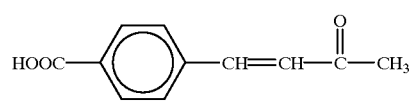

The wavelength-specific sensitizer is produced as summarized below:

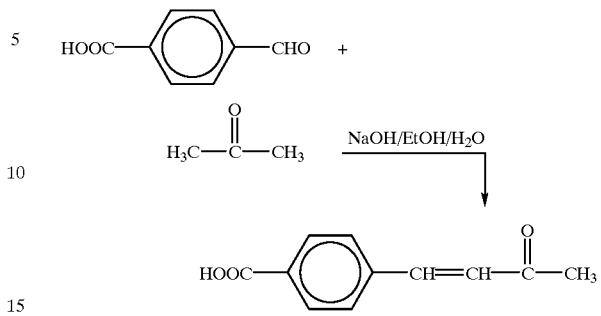

The method of Example 1 is followed except that acetone (Fisher, Optima Grade) is added first, and then the carboxybenzaldehyde is added. More particularly, 32.2 g (0.21 mole) of carboxybenzaldehyde is reacted with 12.2 g (0.21 mole) of acetone in the sodium hydroxide/ethanol/water mixture described in Example 1. Dilute HCl is added to bring the reaction mixture to neutral pH, yielding 37.1 g (91%) of a pale yellow powder which is used without further purification in the following examples.

The resulting reaction product, namely 4-[4'-carboxy phenyl]-3-buten-2-one, had the following physical parameters: Mass. Spec. 190 (m$^+$), 175, 120.

Example 3

This example describes a method of covalently bonding the compound produced in Example 2 to a photoinitiator, namely IRGACURE® 2959 (1-[4-(2-hydroxyethoxy) phenyl]-2-hydroxy-2-methylpropan-1-one or 2-hydroxy-4'-(2-hydroxyethoxy)-2-methylpropiophenone), as is summarized below:

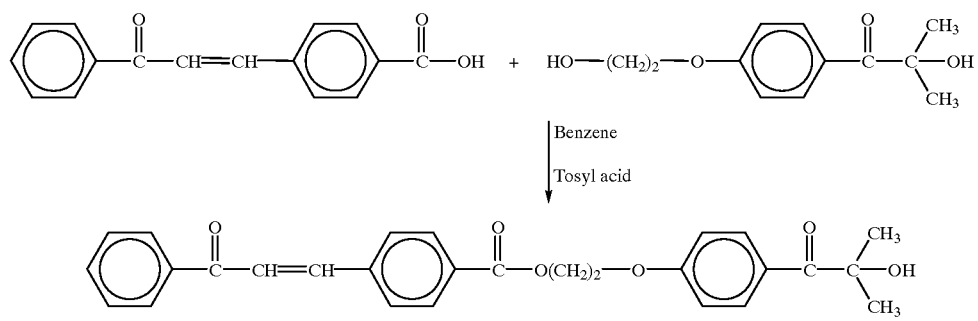

To a 500 ml round bottom flask fitted with a magnetic stir bar, and condenser, is placed 20 g (0.08 mole) of the composition prepared in Example 28, 17.8 g (0.08 mole) IRGACURE 2959 (Ciba-Geigy, N.Y.), 0.5 g p-toluenesulfonic acid (Aldrich), and 300 ml anhydrous benzene (Aldrich). The Dean and Stark adapter is put on the flask and the reaction mixture heated at reflux for 8 hours after which point 1.5 ml of water had been collected (theo.

1.43 ml). The reaction mixture is then cooled and the solvent removed on a rotary evaporator to yield 35.4 g. The crude product is recrystallized from 30% ethyl acetate in hexane to yield 34.2 g (94%) of a white powder.

The resulting reaction product had the following physical parameters: Mass. Spectrum: 458 ($m^+$), 440, 399, 322, 284.

Example 4

The following experiment tested the curing ability of the compound produced in Example 3. More particularly, the compound produced in Example 3 is mixed with the difunctional alkyl urethane acrylate adhesive GENOMER® 1500B (Mader, Biddle Sawyer Corporation, New York, N.Y.) and exposed to 308 nm excimer lamp on a conveyor belt. Two formulations are studied:

Formulation I About 0.05 g of the compound produced in Example 3 is mixed with 10 g of GENOMER® 1500B. Therefore the concentration of the compound produced in Example 3 in the mixture is about 0.5% These components are mixed by means of a magnetic stirring bar at 80° C. A few drops of the mixture is placed on a heated metal plate (Q-Panel Company, Westlake, Ohio) and drawn down to a thickness of about 0.1 mm by means of a 0 draw-down bar (Industry Tech., Oldsmar, Fla.).

Formulation II About 0.025 g of IRGACURE® 2959 is mixed with 10 g of GENOMER® 1500B. These components are mixed and then drawn out on heated metal plates with a 0 draw-down bar as per Formulation I.

Each plate is then exposed to a 308 nanometer excimer lamp on a conveyor belt for approximately 0.8 seconds. The conveyor belt is set at 50 feet/minute. The plate having Formulation I thereon is totally cured upon exposure to the excimer lamp. In contrast, the plate having Formulation II thereon remained tacky and is not fully cured.

Example 5

This example describes the evaluation of the curing behavior of an adhesive containing the wavelength specific photoreactor compositions of Example 3 as reported in Example 4 upon exposure to ultraviolet radiation from an excimer lamp.

An excimer lamp configured substantially as described by Kozelschatz and Eliasson et al., supra, is employed and is shown diagrammatically in FIG. 1. With reference to FIG. 1, the excimer lamp 100 consisted of three coaxial quartz cylinders and two coaxial electrodes. The outer coaxial quartz cylinder 102 is fused at the ends thereof to a central coaxial quartz cylinder 104 to form an annular discharge space 106. An excimer-forming gas mixture is enclosed in the annular discharge space 106. An inner coaxial quartz cylinder 108 is placed within the central cylinder 104. The inner coaxial electrode 110 consisted of a wire wound around the inner cylinder 108. The outer coaxial electrode 112 consisted of a wire mesh having a plurality of openings 114. The inner coaxial electrode 110 and outer coaxial electrode 112 are connected to a high voltage generator 116. Electrical discharge is maintained by applying an alternating high voltage to the coaxial electrodes 110 and 112. The operating frequency is 40 kHz, the operating voltage 10 kV. Cooling water is passed through the inner coaxial quartz cylinder 108, thereby maintaining the temperature at the outer surface of the lamp at less than about 120° C. The resulting ultraviolet radiation is emitted through the openings 114 as shown by lines 118. The lamp is used as an assembly of four lamps 100 mounted side-by-side in a parallel arrangement.

A film of adhesive is deemed cured completely, i.e., through the entire thickness of the film, when it passed the scratch test; see, e.g., M. Braithwaite et al., "Chemistry & Technology of UV & EB Formulation for Coatings, Inks & Paints," Vol. IV, SITA Technology Ltd., London, 1991, pp. 11–12.

Example 6

This example describes a method of covalently bonding two photoinitiators, namely IRGACURE 2959, to a chalcone sensitizer of the present invention, as is summarized below in a two step reaction:

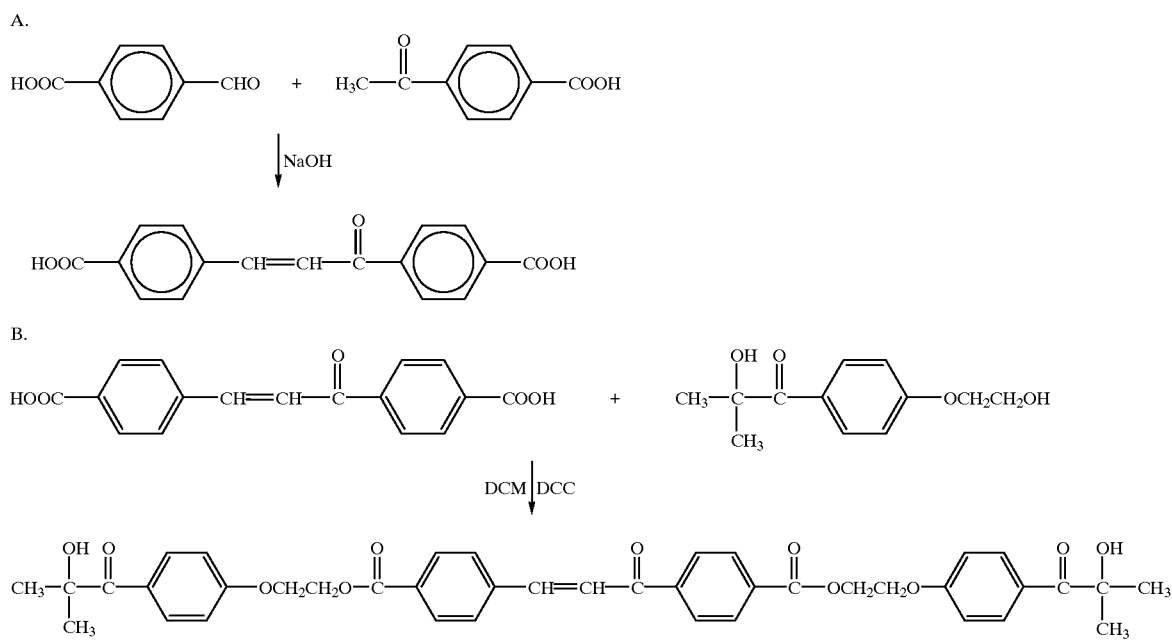

Step A

To a 250 ml round bottom flask fitted with a magnetic stir bar is added 5.4 g sodium hydroxide (Aldrich), 5 ml water, and 45 ml ethanol, and the solution is cooled in a water bath. When the reaction mixture is at room temperature, 15.7 g (0.10 mole) carboxybenzaldehyde (Aldrich), and 17.2 g (0.10 mole) acetylbenzoic acid (Aldrich) are added and the solution stirred overnight (12 hours). The reaction mixture is then chilled in an ice bath and the solution neutralized/acidified with dilute HCl until pH indicator paper showed a pH of 3 to 5. The yellow precipitate is filtered and the solid is dried overnight in a vacuum desiccator. The product of this reaction is the di-carboxylic acid substituted chalcone illustrated above. The yield is 28.1 grams (90%).

Step B

In a 500 ml round bottom flask flushed out by argon is placed a magnetic stir bar, 23.6 g (0.08 mole) of the di-carboxylic acid substituted chalcone produced above in step A, 200 ml of dry dichloromethane (Aldrich), 35.6 g (0.16 mole) IRGACURE 2959 (Ciba-Geigy), and 0.8 g dimethylaminopyridine (Aldrich). The reaction mixture is cooled in an ice bath to 0° C., and then 18.4 g of DCC (Aldrich) is added over 5 minutes and the solution is allowed to warm to room temperature, and is stirred overnight. The reaction mixture is filtered and washed with 0.5 N HCl aqueous followed by saturated NaHCO$_3$ solution. The organic layer is separated, dried (Na$_2$SO$_4$) and the solvent removed under reduced pressure to yield a pale yellow solid. The product is the multi-photoinitiator photoreactor illustrated above. The yield is 51.8 g (91%).

The resultant reaction product had the following physical parameters:

$^1$H NMR [CDCL$_3$] 1.7 [s], 4.0 [d], 4.2 [d], 7.0 [d], 7.2–8.2 [nu]. Note that the ratio of CH$_3$ to CH=CH is 12 to 2, thus indicting that there are two IRGACURE 2959s to one chalcone.

Example 7

The following experiment tested the curing ability of the wavelength specific photoreactor composition produced in Example 6 in comparison to the wavelength specific photoreactor composition produced in Example 3 and to a commercially available photoinitiator product. More particularly, the same formulation to be cured is mixed with a commercial initiator product (3.5% IRGACURE® 907 with 3.5% ITX coinitiator, by weight), or with the wavelength specific photoreactor composition produced in Example 3, or with the wavelength specific photoreactor composition produced in Example 6. Each mixture is drawn into a 50 micron film and then cured. The formulation is an offset press formulation of a high molecular weight urethane acrylate having a molecular weight of above 100,000. Also, as the formulation is thixotropic, the formulation also contains approximately 5% clay.

More specifically, approximately 2 grams of the formulation for offset presses is placed in an aluminum pan and the corresponding weight of the appropriate photoinitiator then added to give a 6 to 7% concentration by weight of the photoinitiator. Table 2 reports the concentrations of each of the photoreactors in their respective formulation mixtures. The mixture is heated on a hot plate set at a low heat and the mixture stirred for five minutes to ensure mixing. A small amount of the mixture is then placed on a Q-Panel (3 inch by 5 inch) plate and drawn down to a film thickness of 50 microns using an 'O' or "3" bar. The plate is then placed under a 308 nm excimer lamp and exposed the light until the mixture is cured, as determined by the scratch and twist test. The excimer lamp has an input power of approximately 2.5 kilowatts, and an output power of approximately 0.1 watt per square centimeter per lamp bulb.

Table 1 summarizes the curing times for the clear coating. As shown below, the wavelength specific photoreactor compositions of the present invention, as produced in Examples 3 and 6, had cure times of only 0.04 seconds, wherein the commercial photoinitiator had a cure time that is 40 times greater, namely, 1.6 seconds.

TABLE 1

| Cured Offset Press Coatings* | Cure Time (Sec) |
|---|---|
| (50 micron film) | |
| Clear Coating (Commercial Initiator) | 1.6 |
| Clear Coating (Example 3 Photoreactor) | 0.04 |
| Clear Coating Example 6 Photoreactor) | 0.04 |

*Paste formulations which contain a clay agent to introduce thixotropic properties Table 2 summarizes the curing times for a pigmented coating, wherein the formulation described above is further admixed with 15% by weight of a green pigment, namely, Gamma Cure. As shown below, the wavelength specific photoreactor composition produced in Example 6 had the shortest curing time, namely, 0.06 seconds. The wavelength specific photoreactor composition produced in Example 3 had a curing time of 0.10 seconds, and the commercial photoinitiator had a cure time that is 50 times greater than the wavelength specific photoreactor composition of Example 6, namely 3.0 seconds.

TABLE 2

| Cured Offset Press Coatings* | Cure Time (Seconds) | Conc. of Photoreactor |
|---|---|---|
| (50 micron film) | | |
| Clear coating (Commercial Initiator) | 3.0 | 7% |
| Clear Coating (Example 3 Photoreactor) | 0.10 | 6% |
| Clear Coating (Example 6 Photoreactor) | 0.06 | 6% |

*Paste formulations which contain a clay agent to introduce thixotropic properties Example 8

The following experiment tested the curing ability of the wavelength specific photoreactor composition produced in Example 6 in comparison to the wavelength specific photoreactor composition produced in Example 3 and to a commercially available photoinitiator product, wherein the power setting for the excimer lamp is varied. With the exception of varying the power setting of the excimer lamp, all other aspects of the experiment are described in Example 7. Table 3 summarizes the curing times for the clear and pigmented formulations, wherein "full" represents full lamp power, "0.75" represents 75% lamp power, etc.

TABLE 3

| Sample | Excimer Lamp Power Setting | | | |
| --- | --- | --- | --- | --- |
| | Full | 0.75 | 0.50 | 0.25 |
| Commercial Initiator 7% | | | | |
| Clear | 1.6 | 2.0 | 2.5 | 4.0 |
| Pigmented | 3.0 | 5.0 | 7.5 | 15.0 |
| Example 3 Photoreactor 6% | | | | |
| Clear | 0.04 | 0.08 | 0.10 | 0.26 |
| Pigmented | 0.10 | 0.14 | 0.22 | 0.34 |
| Example 6 Photoreactor 6% | | | | |
| Clear | 0.04 | 0.06 | 0.12 | 0.16 |
| Pigmented | 0.04 | 0.08 | 0.18 | 0.20 |

Example 9

Examples 9 through 12 describe the synthesis of the wavelength specific photoreactor composition shown as the reaction product in Example 12.

In a 1 liter 3-necked round bottomed flask fitted with a mechanical stirrer and condenser, is placed 200 g (1.56 moles) of cyclohexyl carboxylic acid (Aldrich) and 223 g (1.2 eq) of thionyl chloride (Aldrich). The reaction mixture is stirred and heated to reflux. 50 ml of toluene is added to allow the reaction mixture to become a solution. After 1 hour, 300 ml of dry toluene is added and the solvent is distilled off. 200 ml of toluene with a small amount of thionyl chloride is distilled off and the distillate has a steady boiling point of approximately 110° C. The condenser is then mounted back for reflux and 300 ml of dry toluene is added along with 141 g (1.5 moles) of phenol (Aldrich) and the mixture is refluxed for 12 hours. The solvent is then removed under reduced pressure to leave a pale brown oil. The yield is 287 g (94%).

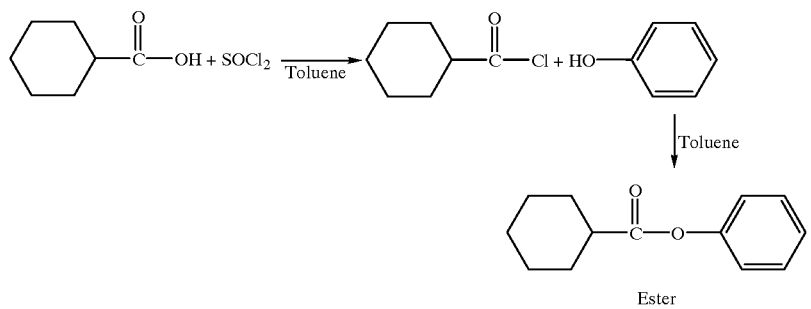

Ester

The resulting reaction product had the following physical parameters:

$^1$H NMR [CDCl$_3$] 1.2–2.8 (m), 1.8 (m), 2.0(m), 6.9–7.5 (m), ppm. HPLC 90% CH$_3$CN/10% H$_2$O—C$_{18}$ Column: Retention time of 5.8 minutes Example 10

To a 1 liter 3-necked round bottom flask fitted with a mechanical stirrer, condenser and flushed with argon, is added 65.2 g of aluminum chloride (Aldrich), 100 ml of carbon disulfide (Aldrich). To this stirred suspension is slowly added 100 g (0.69 moles) of the ester from Example 9. and the mixture is stirred under reflux overnight (12 hours). The mixture is then a thick brown sludge which is broken up by the addition of dilute HCl. The reaction mixture is poured into a separatory funnel and extracted three times with 150 ml each of ether. The ether extracts are combined, washed with ice cold water, dried over MgSO$_4$ and the ether is removed to give 95 g (95% yield) of a thick light brown oil.

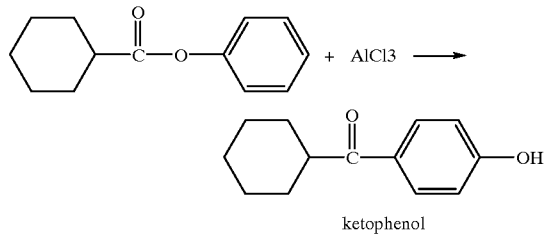

ketophenol

The resulting reaction product had the following physical parameters:

$^1$H NMR [CDCl$_3$] 0.8–2.3 (m), 3.7 (s), 2.0(m), 7.2–7.7 (m), ppm.

Example 11

In a 1 liter, 3 necked round bottomed flask fitted with a mechanical stirrer and a condenser, an inlet gas tube and a bubbler fitted to the condenser, is placed 90 g (0.44 moles) of the ketophenol from Example 10, and 300 ml of dry tetrahydrofuran. The reaction mixture is chilled in a salt/ice bath and 98.5 g (0.88 moles) of potassium t-butoxide is added. After 20 minutes, a stream of dry oxygen is bubbled into the reaction mixture for 2 hours. The reaction mixture is then neutralized with dilute HCl and then extracted three times each with 100 ml of ether. The combined extracts are then washed with water, dried over MgSO$_4$ and the solvent removed under reduced pressure to yield 95.2 g of a thick oil (98% yield).

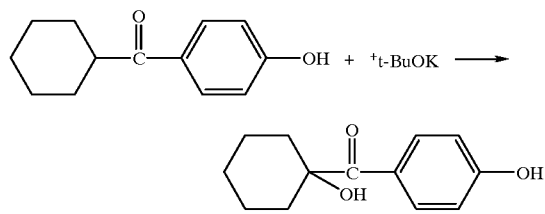

The resulting reaction product had the following physical parameters:

$^1$H NMR [CDCl$_3$] 0.8–2.3 (m), 3.7 (s), 2.0(m), 4.6 (s), 7.2–7.7 (m), ppm.

Example 12

In a 1 liter, 3-necked round bottomed flask fitted with a mechanical stirrer and a condenser is placed 50 g (0.2 moles of the product from Example 6 and 23.6 g (0.2 moles) of thionyl chloride and 50 mls of dry toluene. The reaction mixture is heated to reflux for 2 hours after which the condenser is turned to allow distillation of the toluene and any unreacted thionyl chloride. An additional 150 ml of toluene is added and 100 ml allowed to be distilled giving a steady 110° C. boiling point. 200 ml of fresh, dry toluene is added and the condenser adjusted to its reflux position.

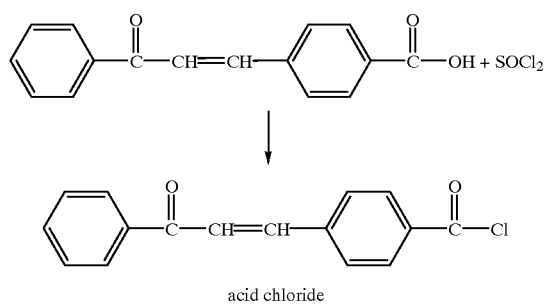

acid chloride

To the reaction mixture is slowly added 44 g (0.2 moles) of the diol from Example 11 and the mixture is allowed to reflux for 12 hours. The solution is then removed under reduced pressure to yield 86.7 g (95% yield) of a light yellow solid. The solid is recrystalized from benzene to yield a yellow crystalline material with a melting point of 127–128° C.

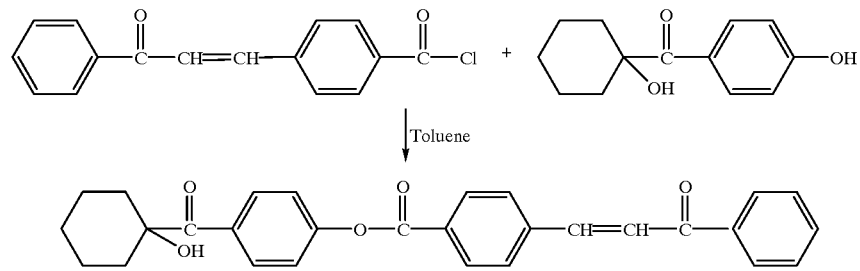

Example 13

Examples 13 through 17 describe the synthesis of the double-wavelength specific sensitizer photoreactor shown as the product in Example 17.

In a 500 ml round bottomed flask fitted with a magnetic stirrer and a condenser is placed 122.1 g of sodium hydroxide, 100 ml of water, and 100 ml of ethanol. The solution is stirred and 125 g (0.73 mole) of ethyl 4-hydroxycyclohexane carboxylate is added. The solution refluxed for 2 hours, cooled and the solution is neutralized with dilute HCl. The solution is then extracted three times with 100 ml of ether (3×100 ml). The ether is separated, dried (MgSO$_4$) and removed under reduced pressure to yield 100 g of a white powder. (95.1% yield)

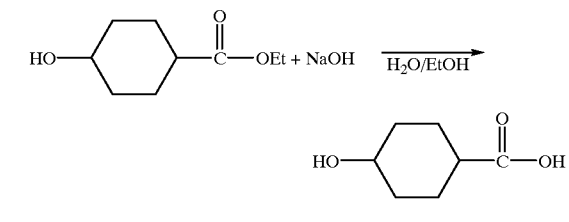

The resulting reaction product had the following physical parameters:

$^1$H NMR [CDCl$_3$] 1.5–1.7 (m), 1.8 (m), 2.0(m), 3.8 (m), 4.8–5.0 (m) ppm.

Example 14

To a 3 necked round bottom flask (500 ml) fitted with a mechanical stirrer and a condenser, is placed 90 g (0.62 moles) of 4-hydroxylcyclohexyl carboxylic acid and 89.2 g of thionyl chloride, and the mixture is stirred for one hour before heating to reflux. On reflux, 80 ml of dry toluene is added and the mixture stirred for an additional hour. 100 ml of toluene is added and the liquid distilled to remove any excess thionyl chloride. After 50 ml is distilled, another 50 ml of toluene is added, and the distillation continued until 120 ml of toluene/thionyl chloride is collected.

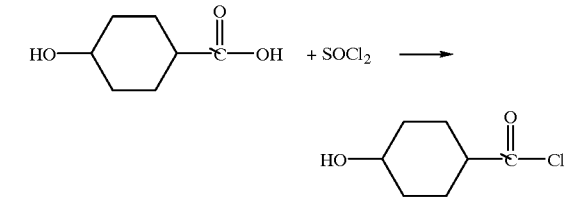

The distillation is stopped and the condenser is fitted for reflux. To the mixture is added 100 ml of toluene and 58.3 g (0.62 moles) of phenol and the reaction mixture refluxed for 12 hours. The solvent is then removed under reduced pressure to yield 113 g (83%) of a light yellow oil.

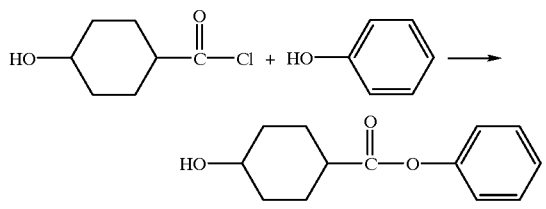

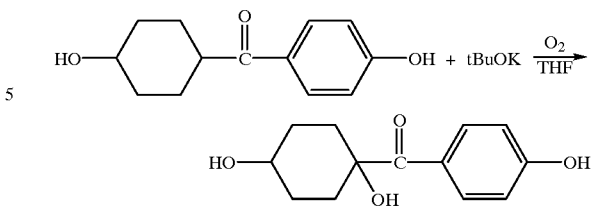

The resulting reaction product had the following physical parameters:

$^1$H NMR [CDCl$_3$] 1.6–3.0 (m), 6.8–7.5 (m) ppm

Example 15

To a 3 necked 500 ml round bottom flask fitted with a mechanical stirrer and a condenser, is placed 60.4 g (0.45 moles) anhydrous aluminum chloride and 100 ml of carbon disulfide. To this mixture is slowly added 100 g (0.45 moles) of the ester from Example 14. The mixture is stirred for one hour and then heated to reflux for eight hours. The reaction is cooled and dilute HCl is added slowly and the mixture stirred for two hours. The reaction mixture is poured into a separatory funnel and extracted three times with 100 ml with The resulting reaction product had the following physical parameters:

$^1$H NMR [CDCl$_3$] 1–3 (m), 6.8–7.6 (m), ppm.

Example 17

To a solution of 183.8 g (0.78 moles) of the acid chloride from Example 12 in 300 ml of toluene in a 2 liter 3-necked flask fitted with a condenser and mechanical stirrer, is added 80.0 g (0.36 moles) of the triol and the solution is refluxed for 8 hours. Removal of the toluene gave a light yellow powder which is recrystallized from benzene to yield 201.1 g (84%) of pale yellow crystals.

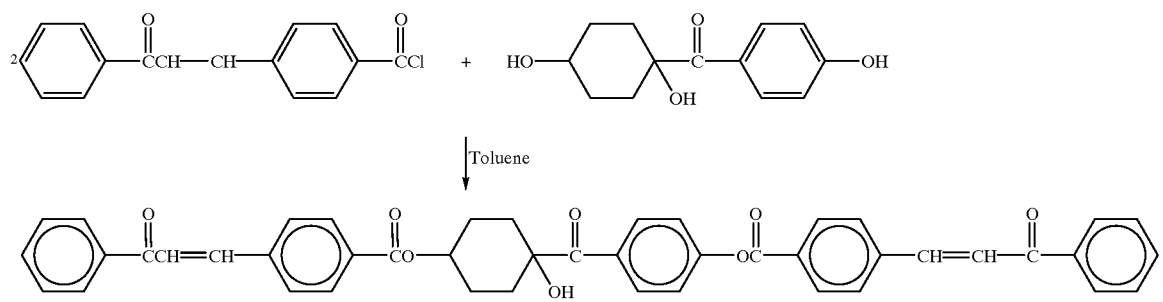

ether. The organic layer is then removed to yield an oil (95 g, 86% yield).

The resulting reaction product had the following physical parameters:

$^1$H NMR [CDCl$_3$] 1–3 (m), 6.8–7.6 (m), ppm.

Example 16

In a 500 ml round bottom flask fitted with a mechanical stirrer and a condenser and being flushed with dry argon is placed 137.8 g (1.23 moles) potassium t-butoxide, 200 ml of dry tetrahydrofuran and the solution chilled in a salt-ice bath. 90 g (0.41 moles) is added and the solution stirred for 30 minutes. Dry air is then bubbled into the solution for 2 hours. The solution is quenched with 50 ml water and neutralized with dilute HCl. The reaction mixture is extracted with ether (3×100 ml), and the ether and solvents removed to yield 90.1 g (93% yield) of the triol.

The resulting reaction product had the following physical parameters:

$^1$H NMR [CDCl$_3$] 1.5–2.8 (m), 7.6–9.7 (m), ppm.

Example 18

The cure rate of off-set press black ink is checked using the new compound from Example 17 under an excimer lamp (308 nm radiation).

1. A 5% wt/wt mixture of 14% black pigmented off-set press ink is made with the compound from Example 17 in an aluminum pan and heated to ensure good mixing. The black ink is drawn out on a hot (60° C.) plate using a zero-draw-down bar to give a film of 20–30 micron thickness. The film is exposed to 0.1 seconds flash of 308 nm excimer lamp radiation and the degree of cure determined by scratch and twist analysis.

The thinner parts of the film had a total cure, and the thicker parts had a skin cure.

2. A 2.5% wt/wt ink is made as previously described and drawn down with the zero draw-down bar. The ink is exposed to 0.1 seconds of 308 nm radiation resulting in a complete cure of the film.

Using a higher concentration (5%) of the compound from Example 17, apparently is too high a concentration and the double antenna system shields the layer before and gives slower curing. It is believed that the antenna system shields the layers below and gives slow curing.

Example 19

This example describes a method of preparing a photoreactor of the present invention. More particularly, this example describes a method for preparing 1-phenyl-4-hydroxy-4-methyl-1-penten-3-one having the following structure:

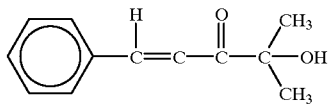

The reaction is summarized as follows:

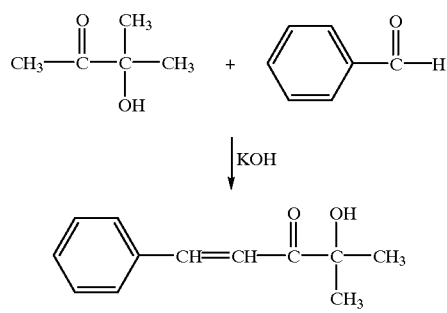

To a 500 ml 3-necked round bottom flask fitted with a magnetic stirrer and condensor, is placed 35.6 g (0.64 moles; 1.3 equivalents) of potassium hydroxide and 500 ml ethanol and 250 ml of water. The flask is cooled in an ice water bath to maintain the flask at 20–25° C. 50.0 g (0.49 mole) of 3-hydroxy-3-methyl-2-butanone (Aldrich) and 52 g (0.49 moles) of freshly distilled benzaldehyde (Aldrich) is added to the flask, and the mixture stirred overnight (12 hours). The solution is then neutralized with dilute HCL using pH paper as an indicator of the pH. The mixture is poured into a separatory funnel (500 ml) and 1 gram of sodium chloride is added to accelerate the separation. The top oil layer is then separated from the water and then placed into a 100 ml round bottom flask. A vacuum distillation is performed which separated off the water, benzaldehyde, and the residue unreacted hydroxybutan-2-one.

Figure 4:
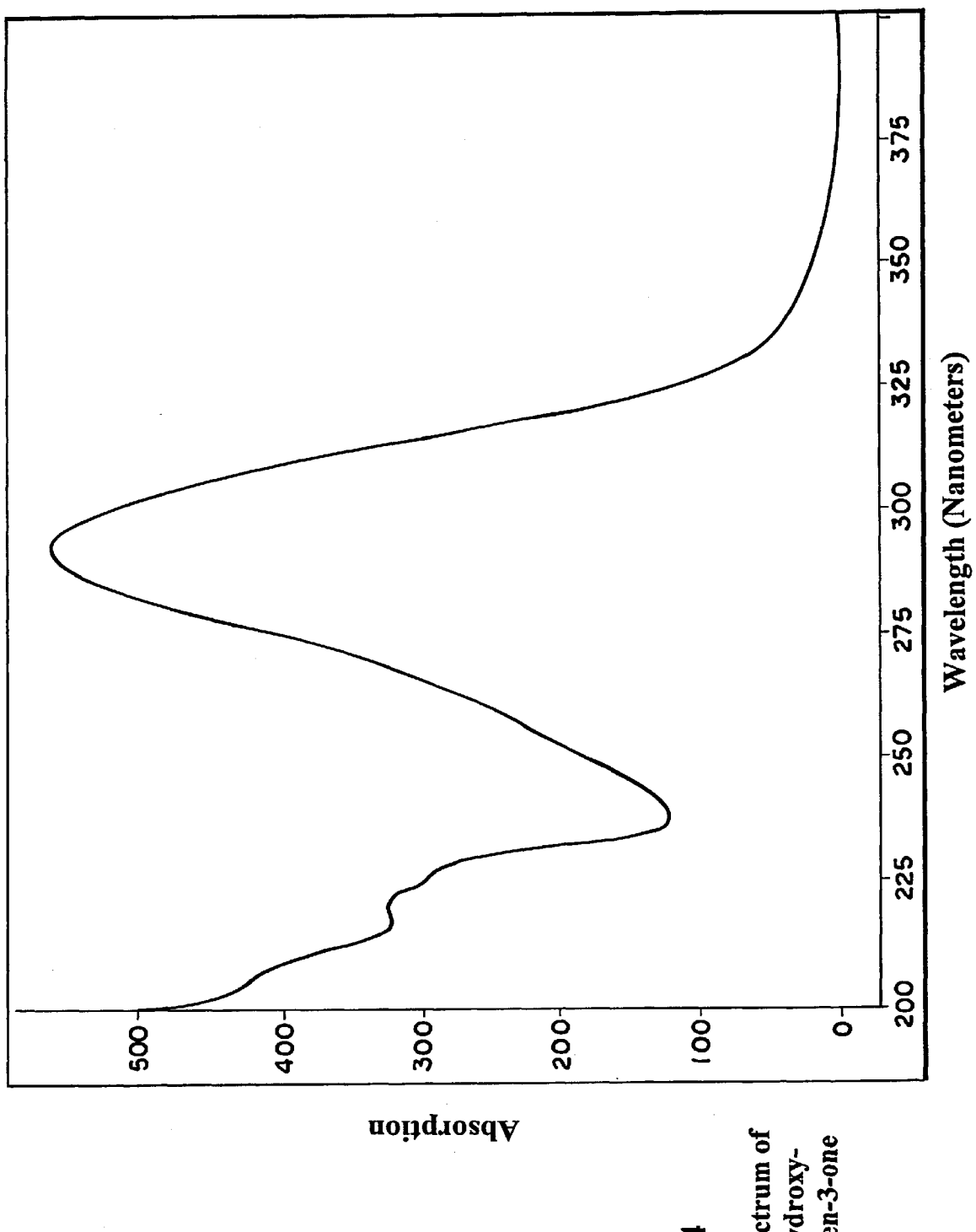
FIG. 4 is the ultraviolet spectrum of the photoreactor prepared in Example 19, namely, 1-phenyl-4-hydroxy-4-methyl-1-penten-3-one.

A pale yellow oil was obtained (Yield 53.1 g (57%) at 155–6° C. at 0.1 mm Hg.) The fractions are listed below:
Fraction 1 boiling point<140° C. at 0.1 mm Hg H$_2$O/alcohol
Fraction 2 boiling point<145–49° C. at 0.1 mm Hg alcohol
Fraction 3 boiling point<155–6° C. at 0.1 mm Hg product+ alcohol
Fraction 4 boiling point<156° C. at 0.1 mm Hg product The resulting product had the following physical parameters:

$^1$H NMR [CDCL$_3$] δ 1.37 [s,6H], 3.93 [s,1H], 2.24[d,1H], 7.37 [m], 7.80 [m], 7.87 [d,1H]

λ$_{max}$ 293 nm (FIG. 4 is the ultraviolet spectrum of 1-phenyl-4-hydroxy-4-methyl-1-penten-3-one)

HPLC C-18 Column, solvent 90% acetonitrile in 10% water, suggests fractions 3 and 4 have small amounts of butanone starting material in them.

Example 20

This example describes the use of the photoreactor prepared in Example 19 to photocure flexographic magenta and black inks (Gamma Graphics, Pa.). The ink is placed in a small aluminum pan and the corresponding % of the photoreactor prepared in Example 19 is added thereto. The ink/photoreactor composition is stirred on a hot plate for 3 minutes and then one drop of the mixture is placed on a metal plate and drawn down with a zero draw-down bar. The mixture is cured using a 308 nm excimer lamp with a flash at 0.05 second setting. The cure is tested by rubbing, and/or pressing and twisting, the cured mixture with a finger.

The results for the magenta ink/photoreactor mixture are as follows. The 4% wt/wt of the photoreactor from Example 19 was fully cured after the 0.05 second flash of the excimer lamp. The 2% wt/wt of the photoreactor from Example 19 was fully cured after the 0.05 second flash of the excimer lamp. The 1% wt/wt of the photoreactor from Example 19 was fully cured after the 0.05 second flash of the excimer lamp.

The results for the black ink/photoreactor mixture are as follows: The 4% wt/wt of the photoreactor from Example 19 was fully cured after the 0.05 second flash of the excimer lamp. A good cure was achieved with the 2% wt/wt of the photoreactor from Example 19 after the 0.05 second flash of the excimer lamp.

Example 21

This example describes the preparation of the photoreactor, 2[p-(2- methyllactoyl)phenoxy]ethyl 1,3-dioxo-2-isoindolineacetate.

A 250 ml, three-necked, round-bottomed flask was fitted with a Dean and Stark apparatus with condenser and two glass stoppers. The flask was charged with 20.5 g (0.1 mole) of phthaloylglycine (Aldrich Chemical Company, Milwaukee. Wis.), 24.6 g (0.1 mole) of IRGACURE® 2959 (a,a-dimethyl-a-hydroxy-4-(2-hydroxyethoxy)acetophenone, Ciba-Geigy Corporation, Hawthorne, N.Y.), 100 ml of benzene (Aldrich), and 0.4 g of p-toluenesulfonic acid (Aldrich). The resulting mixture was heated at reflux temperature for three hours, after which time 1.8 ml (0.1 mole) of water was collected in the Dean and Stark apparatus. The solvent was removed to give 43.1 g of white powder. The powder was recrystallized from 30 volume percent ethyl acetate in hexane (Fisher Scientific, Pittsburgh, Pennsylvania) to give 40.2 g (93 percent yield) of a white crystalline powder having a melting point of 153–4° C.

The expected structure was verified by infrared and nuclear magnetic resonance analyses. The infrared spectrum of the powder was obtained as a Nujol mull and showed absorption maxima at 3440, 1760, 1680, and 1600 cm$^{-1}$. The nuclear magnetic resonance data for the powder were as follows:

$^1$H NMR (CDCl$_3$): 1.64 (s), 4.25 (m), 4.49 (m), 6.92 (m), 7.25 (m), 7.86 (m), 7.98 (m), 8.06 (m) ppm.

Example 22

This example describes the preparation of the photoreactor, 2-hydroxy-2-methyl-4'-[2-[p-(3-oxobutyl) phenoxy]ethoxy]propio-phenone. The preparation was carried out in two steps.

A 100-ml round-bottomed flask was charged with 24.6 g (0.1 mole) of IRGACURE® 2959, 20 ml of toluene (Aldrich), 11.9 g (0.1 mole) of thionyl chloride (Aldrich), and 0.5 ml of pyridine (Aldrich). The flask was fitted with a condenser and the reaction mixture was heated at reflux temperature for two hours. The solvent was removed by distillation at reduced pressure (0.1 Torr) to yield a colorless solid which was used without purification.

To a 250-ml, three-necked, round-bottomed flask fitted with a condenser and a magnetic stirring bar was added 17.6 g (0.1 mole) of 4-(4-hydroxyphenyl)butan-2-one (Aldrich), the chloro-substituted IRGACURE® 2959 (a,a-dimethyl-a-hydroxy-4-(2-chloroethoxy)-acetophenone) prepared as described above, 1.0 ml of pyridine, and 100 ml of anhydrous tetrahydrofuran (Aldrich). The mixture was heated at reflux temperature for three hours and the solvent then was partially (about 60 volume percent) removed under reduced pressure. The remaining mixture was poured into ice water and extracted with two 50-ml aliquots of diethyl ether (Aldrich). The ether extracts were combined and dried over anhydrous magnesium sulfate. Removal of the solvent left 39.1 g of a white solid. Recrystallization of the solid as described in Example 21 gave 36.7 g (91 percent yield) of a white crystalline powder having a melting point of 142–3° C.

The expected structure was verified by infrared and nuclear magnetic resonance analyses. The infrared spectrum of the powder was obtained as a Nujol mull and showed absorption maxima at 3460, 1740, 1700, 1620, and 1600 $cm^{-1}$. The nuclear magnetic resonance data for the powder were as follows:

$^1$H NMR (CDCl$_3$): 1.62 (s), 4.2 (m), 4.5 (m), 6.9 (m) ppm.

Example 23

This example describes the preparation of the photoreactor, [p-[(4-benzoylcyclohexyl)oxy]phenyl]-2-butanone.

To a 250-ml, two-necked, round-bottomed flask fitted with a condenser and a stopper was added 20.4 g (0.1 mole) of IRGACURE 184 (Ciba-Geigy) and 100 ml of anhydrous tetrahydrofuran. The mixture was stirred and cooled to ice/salt bath temperature while flushing the flask with argon. To the resulting solution was added slowly 20.0 g (0.15 mole) of aluminum chloride (Aldrich) over a 40 minute period. The resulting mixture was stirred an additional 20 minutes. To the mixture then was added 17.6 g (0.1 mole) of 4-(4-hydroxyphenyl)butan-2-one. The new mixture was stirred overnight while being allowed to warm to ambient temperature. The reaction mixture then was poured into ice water and extracted with three 50-ml portions of diethyl ether. Removal of the ether gave 34.1 g of a white solid. Recrystallization of the solid from 10 volume percent ethyl acetate in hexane gave 30.2 g (83 percent) of a white crystalline powder having a melting point of 136–8° C.

The expected structure was verified by infrared and nuclear magnetic resonance analyses. The infrared spectrum of the powder was obtained as a Nujol mull and showed absorption maxima at 1760, 1740, 1620, and 1600 $cm^{-1}$. The nuclear magnetic resonance data for the powder were as follows:

$^1$H NMR (CDCl$_3$): 2.10 (s), 2.70 (m), 6.80 (m), 6.92 (m), 8.42 (m) ppm.

Example 24

This example describes the preparation of the photoreactor, 1,3-dioxo-2-isoindolineacetic acid, diester with 2-hydroxy-4'-(2-hydroxyethoxy)2-methylpropiophenone.

A 250-ml, two-necked, round-bottomed flask was fitted with a condenser and a Dean and Stark apparatus. The flask was charged with 41.0 g (0.2 mole) of phthaloylglycine, 24.6 g (0.1 mole) of IRGACURE 2959, 100 ml of benzene, and 3 ml of concentrated sulfuric acid (Fisher). The mixture was heated at reflux temperature for three hours, after which time 3.6 ml (0.2 mole) of water had been collected in the Dean and Stark apparatus. The solvent was removed from the reaction mixture to give 61.8 g of a solid. The material was recrystallized as described in Example 21 to give 57.6 g (93 percent) of product having a melting point of 168–9° C.

The expected structure was verified by infrared and nuclear magnetic resonance analyses. The infrared spectrum of the powder was obtained as a Nujol mull and showed absorption maxima at 1760, 1740, 1620, and 1600 $cm^{-1}$. The nuclear magnetic resonance data for the powder were as follows:

$^1$H NMR (CDCl$_3$): 1.64 (s), 4.25 (m), 4.49 (m), 6.91 (m), 7.30 (m), 7.84 (m), 7.98 (m), 8.06 (m) ppm.

Example 25

This example describes the evaluation of the curing behavior of adhesives containing the photoreactors of Examples 21–24, inclusive, upon exposure to ultraviolet radiation from an excimer lamp. An excimer lamp configured substantially as described in Example 5 was employed and is shown diagrammatically in FIG. 1.

A standard adhesive mixture was prepared by mixing 90 parts by weight of GENOMER® D1500B Difunctional Polyester Urethane Acrylate (Mader, Biddle Sawyer Corporation, New York, N.Y.) and 9 parts of pentaerythritol triacrylate (Polysciences, Inc., Warrington, Pa.). The mixture was stirred by means of a magnetic stirring bar for 20 minutes at 80° C.

To aliquots of the standard adhesive mixture were added the compounds of Examples 21–24, respectively. Two control mixtures were prepared using commercially available photoinitiators, IRGACURE® 907 (a,a-dimethyl-a-morpholino-4-methylthiophenyl-acetophenone or 2-methyl-1-[4-(methylthio)phenyl]-2-morpholino-propanone-1, Ciba-Geigy) as Control A, and IRGACURE 2959 as Control B. In each case, the amount of photoinitiator or photoreactor added was 1 part. Each resulting mixture was stirred thoroughly. A few drops of each mixture were placed on a metal plate (Q-Panel Company, Cleveland, Ohio) and drawn down to a film having a thickness of about 0.6 mil (about 0.015 mm) by means of a draw-down bar (Industry Tech., Oldsmar, Fla). Each film then was exposed to 222 nanometer (nm) ultraviolet radiation emitted by a KrCl* excimer lamp for a period of time sufficient to cure the film (through-cure time).

A film of adhesive was deemed cured completely, i.e., through the entire thickness of the film, when it passed the scratch test; see, e.g., M. Braithwaite et al., "Chemistry & Technology of UV & EB Formulation for Coatings, Inks & Paints," Vol. IV, SITA Technology Ltd., London, 1991, pp. 11–12. The results are summarized in Table 4.

TABLE 4

Summary of Through-Cure Times With Constant Photoreactor Concentration

| Photoreactor | Through-Cure Time (Sec.) |
| --- | --- |
| Control A | 15.0 |
| Control B | 12.4 |
| Example 21 | 2.0 |
| Example 22 | 3.2 |
| Example 23 | 4.6 |
| Example 24 | 2.2 |

Example 26

The procedure of Example 25 was repeated with varying concentrations of photoreactor. The amount of pentaerythritol triacrylate was decreased as required to provide 100 parts of control photoinitiator- or photoreactor-containing adhesive. The results are summarized in Table 5 (the data for a control photoinitiator or photoreactor concentration of 1 percent are from Example 25).

TABLE 5

Summary of Through-Cure Times With Varying Photoreactor Concentrations

| Photoreactor | Through-Cure Time (Sec.) | | | |
|---|---|---|---|---|
| | 1 Percent | 2 Percent | 3 Percent | 4 Percent |
| Control A | 15.0 | 11.0 | 8.0 | 5.0 |
| Control B | 12.4 | 7.4 | 5.8 | 4.0 |
| Example 21 | 2.0 | 1.4 | 0.9 | 0.5 |
| Example 22 | 3.2 | 2.6 | 1.9 | 1.1 |
| Example 23 | 4.6 | 3.9 | 2.7 | 2.0 |
| Example 24 | 2.2 | 1.6 | 1.0 | 0.6 |

Figure 2:
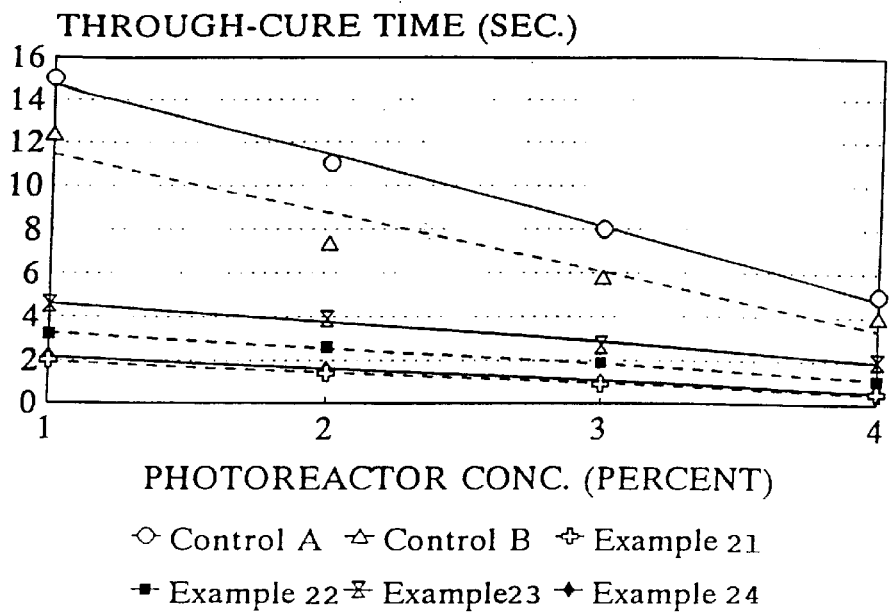
FIG. 2 is a series of plots of control photoinitiator and photoreactor concentration in an adhesive versus through-cure times (radiation exposure times for complete curing) for two control photoinitiators and four photoreactors of the present invention.

While the data in Tables 4 and 5 clearly demonstrate the remarkable improvements in cure rates which are achieved with the photoreactors of the present invention, the data in Table 5 were plotted as photoreactor concentration versus through-cure time. The resulting plots, shown in FIG. 2, dramatically illustrate such remarkable improvements.

Example 27

A series of experiments was carried out as described in Example 25, using only Control B and the photoreactor of Example 21 in order to determine the effect of film thickness on through-cure times. In each case, the concentration of control photoinitiator or photoreactor was 4 weight percent. The results are summarized in Table 6 (the data for a film thickness of 0.6 mil are from Table 4).

TABLE 6

Summary of Through-Cure Times With Varying Film Thicknesses

| Film Thickness | | Through-Cure Time (Sec.) | |
|---|---|---|---|
| Mils | mm | Control B | Example 21 |
| 0.6 | 0.015 | 4.0 | 0.5 |
| 1.0 | 0.025 | 6.1 | 0.8 |
| 2.0 | 0.051 | 14.2 | 1.4 |
| 3.0 | 0.076 | 21.0 | 2.0 |

Figure 3:
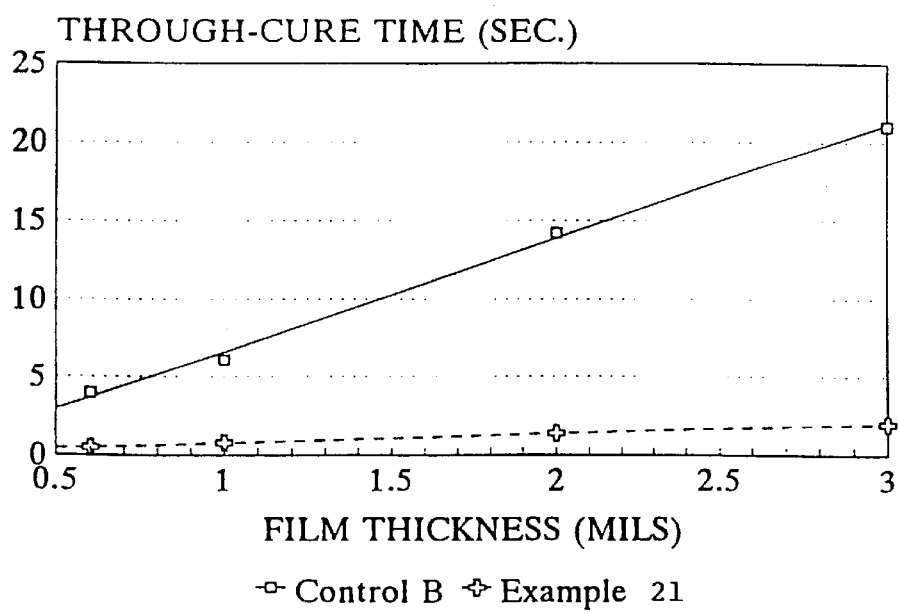
FIG. 3 consists of plots of through-cure times for a control photoinitiator and a photoreactor of the present invention at a constant concentration in an adhesive versus film thickness.

Regardless of the film thickness employed, the photoreactor of Example 21 clearly provided much faster curing rates. In order to better visualize the extent of improvement and any trends which may be present, the data of Table 6 were plotted as film thickness in mils versus through-cure times. The plots are shown in FIG. 3. While it is evident that film thickness affects through-cure time approximately linearly in each case, the rate of increase with increasing film thickness for the control photoinitiator is much greater than for the photoreactor of Example 21.

It may be noted that, because of the high molar absorptivity of the photoreactors of the present invention, film thickness/cure limitations may be observed with very thick film thicknesses. For example, a 25 mil (about 0.64 mm) adhesive film containing the photoreactor of Example 21 remained tacky on the side adjacent to the metal plate supporting the film, even though the upper surface, or top of the film, passed the scratch test.

Example 28

The procedure of Example 21 was repeated with Control A, Control B, and the photoreactor of Example 21 in order to test the curing behavior of the films upon exposure to the radiation from another ultraviolet light source. In this case, a 550-watt, wide spectrum emission, Hanovia medium pressure mercury lamp (Hanovia Lamp Co., Newark, N.J.) was employed in place of the excimer lamp. The distance from the lamp to the sample being irradiated was about 16 inches (about 41 cm). The results are summarized in Table 7.

TABLE 7

Summary of Results with Medium Pressure Mercury Lamp

| Photoreactor | Through-Cure Time |
|---|---|
| Control A | 60 seconds |
| Control B | 90 seconds |
| Example 21 | 15 seconds |

The superiority of the photoreactors of the present invention over known photoinitiators is clear, even when the radiation is not the essentially monochromatic emission which is characteristic of an excimer lamp. The effective tuning of the photoreactor for a specific wavelength band permits the photoreactor to more efficiently utilize any radiation in the emission spectrum of the radiating source corresponding to the "tuned" wavelength band, even though the intensity of such radiation may be much lower than, for example, radiation from a narrow band emitter such as an excimer lamp. In other words, the effectiveness of the photoreactor of the present invention is not dependent upon the availability or use of a narrow wavelength band radiation source.

Example 29

Finally, the procedure of Example 25 was repeated using simple mixtures of sensitizer and photoinitiator. Two mixtures were studied. The first (Mixture A) consisted of Control A and phthaloylglycine, each being present at a level in the adhesive of 1 weight percent. The second mixture (Mixture B) consisted of Control B and phthaloylglycine; again, each component was present at a level of 1 weight percent. The results are summarized in Table 8.

TABLE 8

Summary of Results with Mixtures of Sensitizer and Photoinitiator

| Mixture | Through-Cure Time |
|---|---|
| A | 12.8 seconds |
| B | 10.1 seconds |

It will be remembered from Table 4 of Example 25 that the through-cure times for Controls A and B at levels of 1 weight percent were 15.0 and 12.4 seconds, respectively. It likewise will be remembered that the through-cure time for the photoreactor of Example 21, also present at a level of 1 weight percent, was 2.0 seconds. Given the fact that each of the components in the mixtures summarized in Table 8 was present at a level of 1 weight percent, it is evident that mixtures of the sensitizers and photoinitiators in these Examples are essentially no more effective than the photoinitiator alone. Thus, the unique results obtained with the photoreactors of these Examples were dependent upon the covalent bonding of the sensitizer to the free radical generating photoinitiator. Nevertheless, it is believed that physical mixtures of the sensitizer and photoinitiator are capable of results better than those achievable with photoinitiator alone. It is postulated that such mixtures may be optimized by improving the blending and/or the amounts of the two components.

Example 30

This example describes another method of synthesizing the following wavelength-specific sensitizer:

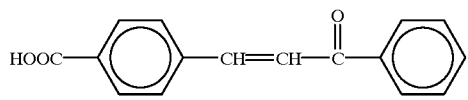

To a 2000 ml round bottom flask fitted with a mechanical stirrer, and a condenser, is added 106 g (1.9 mole) potassium hydroxide (Aldrich), 500 g water and 300 g ethanol. The solution is stirred while being cooled to 20 to 25° C. in an ice bath. To the stirred solution is added 104 g (0.86 mole) acetophenone (Aldrich) and then 130 g (0.86 mole) 4-carboxybenzaldehyde (Aldrich). The reaction mixture is stirred at room temperature for approximately 3–4 hours. The reaction mixture temperature is checked in order to prevent it from exceeding 30° C. Next, dilute HCl is added to bring the mixture to neutral pH as indicated by universal pH indicator paper. The white/yellow precipitate is filtered using a Buchner funnel to yield 162.0 g (75%) after drying on a rotary pump for four hours. The product is used below without further purification.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wavelength specific photoreactor compound having the following formula:

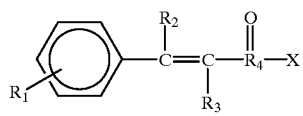

wherein $R_1$ is hydrogen, an alkyl, alkenyl, cycloalkyl, aryl, heteroaryl group, or carboxylic acid group;

$R_2$ is a hydrogen, alkyl, cycloalkyl, or a heterocycloalkyl group;

$R_3$ is a hydrogen, alkyl, cycloalkyl, or a heterocycloalkyl group;

$R_4$ is a carbon or sulfur atom; and wherein X is a reactive-species generating photoinitiator moiety having the following structure:

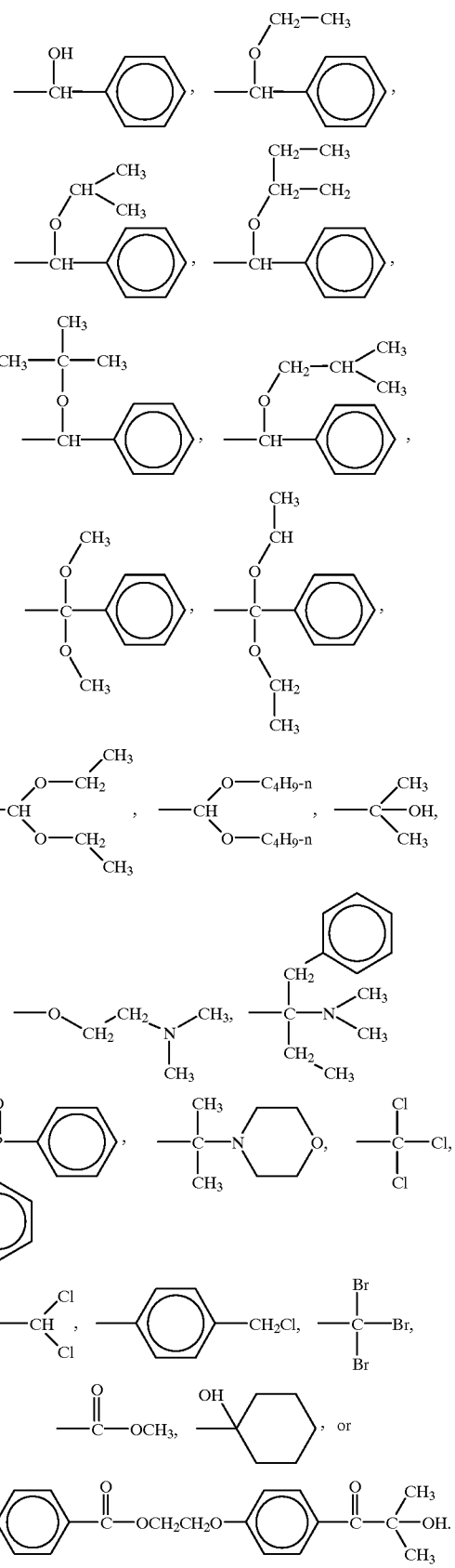

2. The compound of claim 1, wherein $R_4$ is a sulfur atom.

3. The compound of claim 1, wherein $R_4$ is a carbon atom.

4. The compound of claim 3, wherein $R_1$, $R_2$, and $R_3$ are hydrogen.

5. A method of generating a reactive species, comprising irradiating the photoreactor compound of claim 4 with ultraviolet radiation.

6. A method of polymerizing an unsaturated polymerizable material, comprising irradiating an admixture of an unsaturated polymerizable material and the photoreactor compound of claim 4.

7. A polymer film, produced by the process of:
providing an admixture of an unsaturated polymerizable material and the photoreactor compound of claim 4 that has been formed into a film; and
irradiating the film with an amount of radiation sufficient to polymerize the compound polymerizable material.

8. A method of coating a nonwoven web comprising:
providing a nonwoven web coated with an admixture of unsaturated polymerizable material and the photoreactor compound of claim 4; and
irradiating the coating on the web with an amount of radiation sufficient to polymerize the compound polymerizable material.

9. A method of coating a nonwoven web comprising:
providing a nonwoven web coated with an admixture of unsaturated polymerizable material and the photoreactor compound of claim 4; and
irradiating the coating on the web with an amount of radiation sufficient to polymerize the polymerizable material.

10. A method of generating a reactive species, comprising irradiating the photoreactor compound of claim 1 with ultraviolet radiation.

11. A method of polymerizing an unsaturated polymerizable material, comprising irradiating an admixture of an unsaturated polymerizable material and the photoreactor compound of claim 1.

12. A polymer film, produced by the process of:
providing an admixture of an unsaturated polymerizable material and the photoreactor compound of claim 1 that has been formed into a film; and
irradiating the film with an amount of radiation sufficient to polymerize the compound polymerizable material.

13. A method of coating a nonwoven web comprising:
providing a nonwoven web coated with an admixture of unsaturated polymerizable material and the photoreactor compound of claim 1; and
irradiating the coating on the web with an amount of radiation sufficient to polymerize the compound polymerizable material.

14. A method of coating a fiber comprising:
providing a fiber coated with an admixture of unsaturated polymerizable material and the photoreactor compound of claim 1; and
irradiating the coating on the fiber with an amount of radiation sufficient to polymerize the polymerizable material.

15. A wavelength specific photoreactor compound having the following formula:

wherein X is a reactive-species generating photoinitiator moiety;

wherein $R_1$ is hydrogen, an alkyl, alkenyl, cycloalkyl, heterocycloalkyl, aryl, heteroaryl group, or carbonyl group;

$R_2$ is a hydrogen, alkyl, cycloalkyl, or a heterocycloalkyl group;

$R_3$ is a hydrogen, alkyl, cycloalkyl, or a heterocycloalkyl group; and $R_4$ is a sulfur atom.

16. The compound of claim 15, wherein X has the following structure:

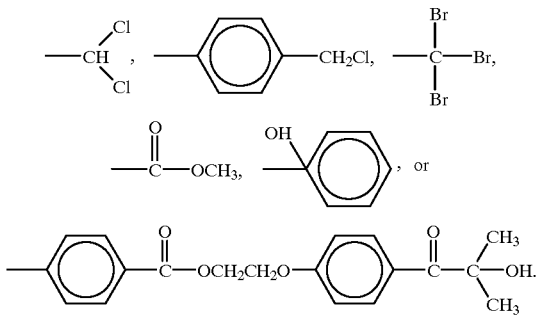

17. A method of generating a reactive species, comprising:
    irradiating the photoreactor compound of claim 15 with ultraviolet radiation.
18. A method of polymerizing an unsaturated polymerizable material, comprising:
    irradiating an admixture of an unsaturated polymerizable material and the photoreactor compound of claim 15.
19. A polymer film, produced by the process of:
    providing an admixture of an unsaturated polymerizable material and the photoreactor compound of claim 15 that has been formed into a film; and
    irradiating the film with an amount of radiation sufficient to polymerize the polymerizable material.
20. A method of coating a nonwoven web comprising:
    providing a nonwoven web coated with an admire of unsaturated polymerizable material and the photoreactor compound of claim 15; and
    irradiating the coating on the web with an amount of radiation sufficient to polymerize the polymerizable material.
21. A method of coating a fiber comprising:
    providing a fiber coated with an admixture of unsaturated polymerizable material and the photoreactor compound of claim 15; and
    irradiating the coating on the fiber with an amount of radiation sufficient to polymerize the polymerizable material.

22. A wavelength specific photoreactor consisting of

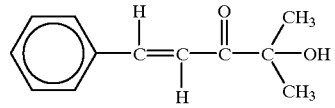

23. A method of generating a reactive species, comprising:
    irradiating the photoreactor of claim 22 with ultraviolet radiation.
24. A method of polymerizing an unsaturated polymerizable material, comprising:
    irradiating an admixture of an unsaturated polymerizable material and the photoreactor of claim 22.
25. A polymer film, produced by the process of:
    providing an admixture of an unsaturated polymerizable material and the photoreactor of claim 22 that has been drawn into a film; and
    irradiating the film with an amount of radiation sufficient to polymerize the polymerizable material.
26. A method of coating a fiber comprising:
    providing a fiber coated with an admixture of unsaturated polymerizable material and the photoreactor of claim 22, and
    irradiating the coating on the with an amount of radiation sufficient to polymerize the polymerizable material.
27. A method of coating a fiber comprising:
    providing a fiber coated with an admixture of unsaturated polymerizable material and the photoreactor of claim 22, and
    irradiating the coating on the with an amount of radiation sufficient to polymerize the polymerizable material.

* * * * *